United States Patent
Vasudevan et al.

(10) Patent No.: US 7,351,737 B2
(45) Date of Patent: *Apr. 1, 2008

(54) 4-[(8-SUBSTITUTED)-6-CHROMANOYL]-AND 4-[8-SUBSTITUTED)-CHROMAN-6-YL-ETHYNYL]-BENZOIC AND PHENYLACETIC ACIDS, THEIR ESTERS AND SALTS HAVING CYTOCHROME P450RAI INHIBITORY ACTIVITY

(75) Inventors: Jayasree Vasudevan, Anaheim, CA (US); Liming Wang, Irvine, CA (US); Xiaoxia Liu, Tustin, CA (US); Kwok-Yin Tsang, Irvine, CA (US); Yang-Dar Yuan, Irvine, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 552 days.

This patent is subject to a terminal disclaimer.

(21) Appl. No.: 10/389,071

(22) Filed: Mar. 14, 2003

(65) Prior Publication Data
US 2003/0207937 A1 Nov. 6, 2003

Related U.S. Application Data

(63) Continuation-in-part of application No. 10/100,638, filed on Mar. 19, 2002, now Pat. No. 6,740,676.

(51) Int. Cl.
*A61K 31/352* (2006.01)
*C07D 311/76* (2006.01)

(52) U.S. Cl. ........................ 514/456; 549/398; 549/405
(58) Field of Classification Search ................ 514/456, 514/183, 449, 451, 453, 454
See application file for complete search history.

(56) References Cited

U.S. PATENT DOCUMENTS

| | | | |
|---|---|---|---|
| 4,658,065 A * | 4/1987 | Aoshima et al. | 564/487 |
| 4,980,369 A * | 12/1990 | Chandraratna | 514/432 |
| 5,399,561 A | 3/1995 | Chandraratna | |
| 5,455,265 A | 10/1995 | Chandraratna | |
| 5,466,861 A | 11/1995 | Dawson et al. | |
| 5,663,347 A | 9/1997 | Chandaratna | |
| 5,675,024 A | 10/1997 | Teng et al. | |
| 5,965,606 A | 10/1999 | Teng et al. | |
| 6,252,090 B1 * | 6/2001 | Vasudevan et al. | 549/23 |
| 6,303,785 B1 * | 10/2001 | Vasudevan et al. | 546/144 |
| 6,313,107 B1 | 11/2001 | Vasuvedan et al. | |
| 6,740,676 B2 * | 5/2004 | Vasudevan et al. | 514/456 |
| 6,864,367 B2 * | 3/2005 | Ikemoto et al. | 540/476 |
| 2004/0043044 A1 * | 3/2004 | Granger et al. | 424/401 |
| 2004/0077721 A1 * | 4/2004 | Yuan et al. | 514/559 |

FOREIGN PATENT DOCUMENTS

| | | |
|---|---|---|
| DE | 33-16932 | 5/1982 |
| DE | 37-08060 | 3/1986 |
| EP | 01-30795 | 1/1985 |
| WO | WO-85-00806 | 2/1985 |
| WO | WO-93-11755 | 6/1993 |
| WO | WO-95-04036 | 2/1995 |

OTHER PUBLICATIONS

Orfanos CE et al. "Current use and future protential role of retinoids in dermatology," Mar. 1997 Drugs 53(3): 358-388.*
Allegretto et al. J. Biol. Chem. 268, 26625-26633.
Bligh et al. Canadian Journal of Biochemistry 37, 911-917 (1959).
Cheng et al. Biochemical Pharmacology vol. 22 pp. 3099-3108.
Dawson, et al. "Chemistry and Biology of Synthetic Retinoids", published by CRC Press, Inc., (1990), pp. 324-356.
De Porre, et al., "Second Generation Retinoic Acid Metabolism Blocking Agent (Ramba) R116010: Dose Finding in Healthy Male Volunteers", University of Leuven, Belgium, pp. 30.
Eyrolles et al., *J. Med. Chem.*, (1994), 37 1508, 1517.
Feigner P.L. and Holm M. (1989) Focus, 112.
Hanzlik, et al., "Cycloprapylamines as Suicide Substrates for Cytochromes P450RAI", *Journal of Medicinal Chemistry* (1979), vol. 22, No. 7, pp. 759-761.
Hanzlik, et al. "Sucidal Inactivation of Cytochrome P450RAI by Cyclopropylamines-Evidence for Cation-Radical Intermediates", *J. Am. Chem. Soc.*, (1982), vol. 104, No. 107, pp. 2048-2052.
Heyman et al. Cell 68, 397-406 (1992).
Kagechika, et al., *J. Med. Chem.*, (1988), 31, 2182-2192.
Kang, et al., "Liarozole Inhibits Human Epidermal Retinoid Acid 4-Hydroxylase Activity and Differentially Augments Human Skin Response to Retinoic Acid and Retinol In vivo", *The Journal of Investigative Dermatology*, (Aug. 1996) vol. 107, No. 2: pp. 183-187.
Kuijpers, et al., The effects of oral liarozole on epidermal proliferation and differentiation in severe plaque psorasis are comparable with those of acitretin, *British Journal of Dermatology*, (1998) 139: pp. 380-389.

(Continued)

Primary Examiner—Phyllis G. Spivack
(74) Attorney, Agent, or Firm—Gabor L. Szekeres

(57) ABSTRACT

Compounds of the formula

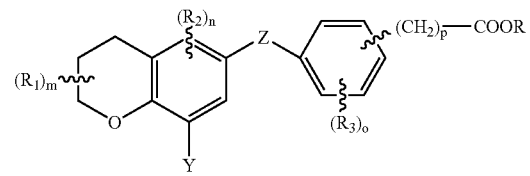

where the variables are defined in the specification have cytochrome P450RAI-1 and P450RAI-2 inhibitory activity, and are suitable for treatment of mammals with conditions which are treatable with retinoids, or which are controlled by or responsive to the organism's native retinoic acid. Formulations containing the compounds of the invention can also be co-administered with retinoids and/or Vitamin A to enhance or prolong the effects of medications containing retinoids, Vitamin A, or of the organism's native retinoic acid.

38 Claims, 1 Drawing Sheet

OTHER PUBLICATIONS

Figure 1:
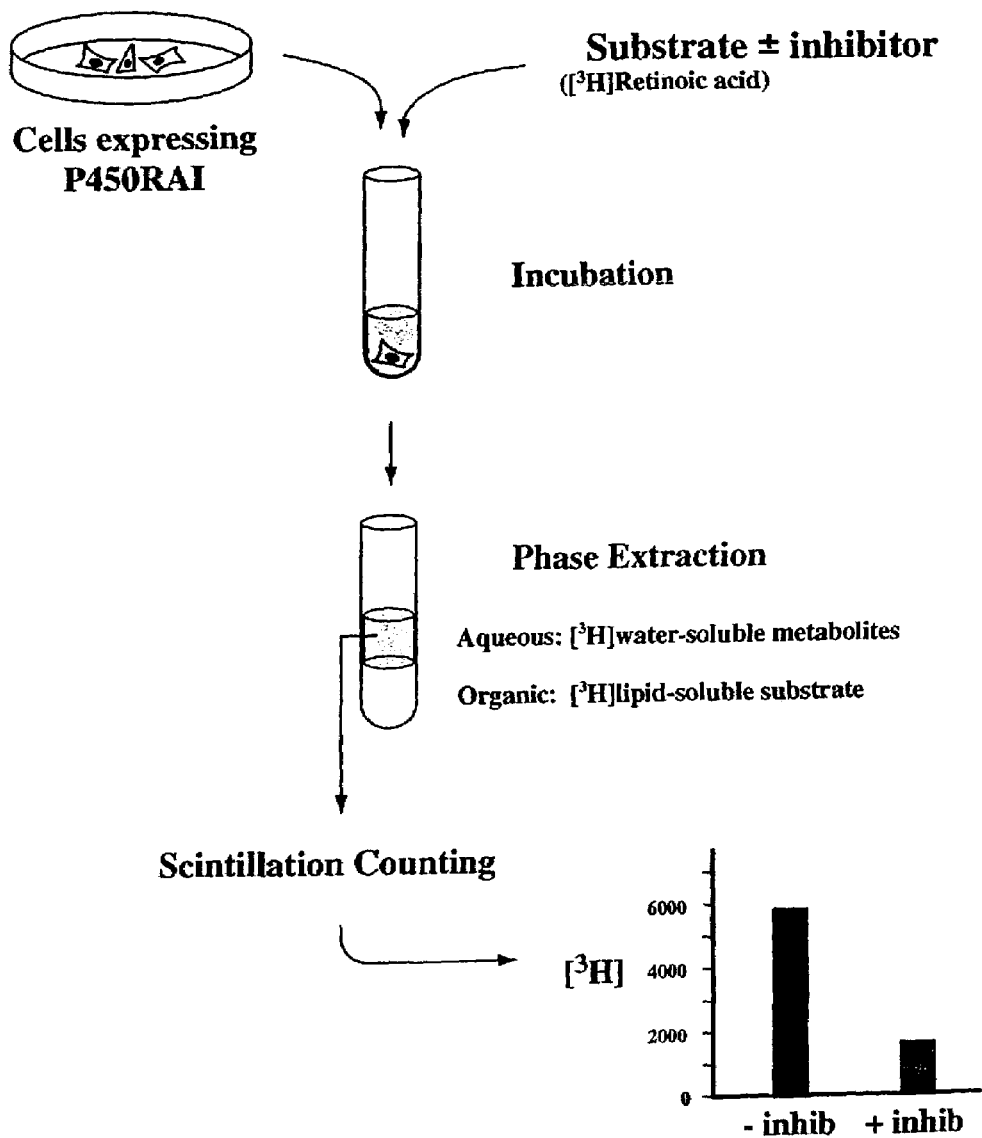

Mangelsdorf et al. The Retinoids: Biology, Chemistry and Medicine, pp. 319-349, Raven Press Ltd., New York.

Ortiz de Montellano, "Topics in Biology—The Inactivation of Chtochrome P450RAI", *Annual Reports in Medicinal Chemistry*, (1984), Chapter 20, pp. 201-210.

Wauwe, et al., "Liarozole, an Inhibitor of Retinoic Acid Metabolism, Experts Retinoid-Mimetic Effects in Vivo", *The Journal of Pharmacology and Experimental Therapeutics*, (1992) vol. 245, No. 2: pp. 718-722.

White, et al., "cDNA Cloning of Human Retinoic Acid-metabolizing Enzyme (hP450RAI) Identifies a Novel Family of Cytochromes P450 (CYP26)*", *The Journal of Biological Chemistry*, (1997) vol. 272, No. 30, Issue of Jul. 25, pp. 18538-18541.

White, et al. "Identification of the human cytochrome P450, P450RAI-2, which is predominantly expressed in the adult cerebellum and is responsible for all trans retinoic acid metabolism," *Proc. Natl. Acad. Sci. USA* vol. 97 No. 12 pp. 6403-6408 (Jun. 6, 2000).

van Wauwe, et al., Ketoconazole Inhibits the in vitro and in vivo Metabolism of All-Trans-Retinoic Acid, *The Journal of Pharmacology and Experimental Therapeutics*, 245(2): 718-722 (1988).

Cheng, et al., "Relationship Between the Inhibition Constant (KI) and the Concentration of Inhibitor which Causes 50 per cent Inhibition (I50) of an Enzymatic Reaction," Biochemical Pharmacology, 22(23): 3099-3108 (1973).

* cited by examiner

4-[(8-SUBSTITUTED)-6-CHROMANOYL]-AND 4-[8-SUBSTITUTED)-CHROMAN-6-YL-ETHYNYL]-BENZOIC AND PHENYLACETIC ACIDS, THEIR ESTERS AND SALTS HAVING CYTOCHROME P450RAI INHIBITORY ACTIVITY

CROSS-REFERENCE TO RELATED APPLICATION

The present application is a continuation in part of application Ser. No. 10/100,638 filed on Mar. 19, 2002 now U.S. Pat. No. 6,740,676.

BACKGROUND OF THE INVENTION

1. Field of the Invention

The present invention is directed to novel compounds that inhibit the enzyme cytochrome P450RAI. More particularly, the present invention is directed to 4-[(8-substituted)-6-chromanoyl]- and 4-[8-substituted)-chroman-6-yl-ethynyl]-benzoic and phenylacetic acids, their esters and salts which inhibit either the enzyme cytochrome P450RAI1 or the enzyme cytochrome P450RAI2, or both enzymes.

2. Background Art

Compounds that have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as $Minoxidil^R$, diseases associated with the immune system, including use of the present compounds as immunosuppressants and immunostimulants, modulation of organ transplant rejection and facilitation of wound healing, including modulation of chelosis. Retinoid compounds have relatively recently been also discovered to be useful for treating type II non-insulin dependent diabetes mellitus (NIDDM).

Several compounds having retinoid-like activity are actually marketed under appropriate regulatory approvals in the United States of America and elsewhere as medicaments for the treatment of several diseases responsive to treatment with retinoids. Retinoic acid (RA) itself is a natural product, biosynthesized and present in a multitude of human and mammalian tissues and is known to play an important rule in the regulation of gene expression, tissue differentiation and other important biological processes in mammals including humans. Relatively recently it has been discovered that a catabolic pathway in mammals, including humans, of natural retinoic acid includes a step of hydroxylation of RA catalyzed by the enzyme Cytochrome P450RAI (retinoic acid inducible). In fact, in the present state of the art it is known that at least two sub-species of cytochrome P450RAI enzymes exist, and these are termed P450RAI1 and P450RAI2. White et al. Identification of the human cytochrome P450), P450RAI-2, which is predominantly expressed in the adult cerebellum and is responsible for all trans retinoic acid metabolism, *Proc. Natl. Acad. Sci. USA* Volume 97 No. 12 pp6403 6408 (Jun. 6, 2000).

Several inhibitors of cytochrome P450RAI have been synthesized or discovered in the prior art, including the well known ketoconazole, liarozole and R116010 compounds. The chemical structures of these prior art compounds are provided below. Relatively recently issued U.S. Pat. No. 6,313,107 describes a number of compounds having cytochrome P450RAI inhibitory activity, and several compounds of this disclosure are substituted chroman derivatives.

It has also been noted in the prior art, that administration to mammals, including humans, of certain inhibitors of CP-450RAI results in significant increase in endogeneous RA levels, and further that treatment with CP450RAI inhibitors, for example with liarozole, gives rise to effects similar to treatment by retinoids, for example amelioration of psoriasis.

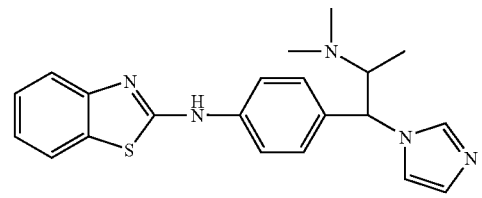

R116010

-continued

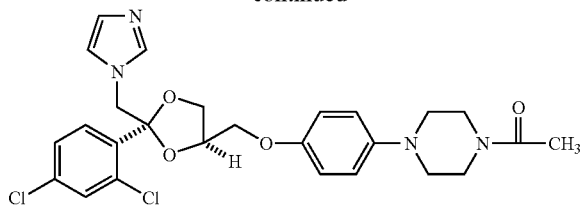

KETOCONAZOLE

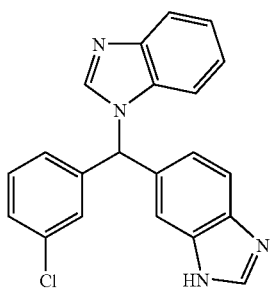

LIAROZOLE

The following publications describe or relate to the above-summarized role of CP450RAI in the natural catabolism of RA, to inhibitors of CP-450RAI and to in vitro and in vivo experiments which demonstrate that inhibition of CP450RAI activity results in a increases indogeneous RA levels and potential therapeutic benefits:

Kuijpers, et al., "The effects of oral liarozole on epidermal proliferation and differentiation in severe plaque psoriasis are comparable with those of acitretin", *British Journal of Dermatology*, (1998) 139: pp 380-389.

Kang, et al., "Liarozole Inhibits Human Epidermal Retinoid Acid 4-Hydroxylase Activity and Differentially Augments Human Skin Responses to Retinoic Acid and Retinol In Vivo", *The Journal of Investigative Dermatology*, (August 1996) Vol. 107, No. 2: pp 183-187.

Vorn Wauwe, et al., "Liarozole, an Inhibitor of Retinoic Acid Metabolism, Exerts Retinoid-Mimetic Effects in Vivo", *The Journal of Pharmacology and Experimental Therapeutics*, (1992) Vol. 261, No 2: pp 773-779.

De Porre, et al., "Second Generation Retinoic Acid Metabolism Blocking Agent (Ramba) R116010: Dose Finding in Healthy Male Volunteers", University of Leuven, Belgium, pp 30.

Wauwe, et al., "Ketoconazole Inhibits the in Vitro and in Vivo Metabolism of All-Trans-Retinoic Acid", *The Journal of Pharmacology and Experimental Therapeutics*, (1988) Vol. 245, No. 2: pp 718-722.

White, et al., "cDNA Cloning of Human Retinoic Acid-metabolizing Enzyme (hP450RAI) Identifies a Novel Family of Cytochromes P450 (CYP26)*", *The Journal of Biological Chemistry*, (1997) Vol. 272, No. 30, Issue of July 25 pp 18538-18541.

Hanzlik, et al., "Cyclopropylamines as Suicide Substrates for Cytochromes P450RAI", *Journal of Medicinal Chemistry* (1979), Vol. 22, No. 7, pp 759-761.

Ortiz de Montellano, "Topics in Biology—The Inactivation of Cytochrome P450RAI", *Annual Reports in Medicinal Chemistry*, (1984), Chapter 20, pp 201-210.

Hanzlik, et al. "Suicidal Inactivation of Cytochrome P450RAI by Cyclopropylamines—Evidence for Cation-Radical Intermediates", *J. Am. Chem. Soc.*, (1982), Vol. 104, No. 107, pp. 2048-2052. White et al. *Proc. Natl. Acad. Sci. USA* supra.

The present invention provides several new 8-substituted chroman compounds which act as inhibitors of CP450RAI1 and or of CP450RAI2, or both, and as such potentially provide therapeutic benefit in the treatment or prevention of the diseases and conditions which respond to treatment by retinoids and or which in healthy mammals, including humans, are controlled by natural retinoic acid. The perceived mode of action of these compounds is that by inhibiting the enzyme CP450RAI that catabolizes natural RA, endogenous RA level is elevated to a level where desired therapeutic benefits are attained. The chemical structures of the compounds of the invention are summarized in Formula 1 in the Summary Section of this application for patent. Beyond the references already mentioned above, based on CP450RAI inhibitory activity or chemical structure the following art is of interest as background to the invention.

U.S. Pat. Nos. 6,313,107; 6,303,785, 5,965,606; 5,675,024; 5,663,347; 5,045,551; 5,023,341; 5,264,578; 5,089,509; 5,134,159; 5,346,895; 5,346,915; 5,149,705; 5,399,561; 4,980,369; 4,826,984; 5,037,825; 5,466,861; WO 85/00806; WO 95/04036; EP 0 130,795; DE 3316932; DE 3708060; Eyrolles et al., *J. Med. Chem.*, (1994), 37 1508, 1517; Kagechika, et al., *J. Med. Chem.*, (1988), 31, 2182-2192; Dawson, et al. "Chemistry and Biology of Synthetic Retinoids", published by *CRC Press Inc.*, (1990), pages 324-356.

SUMMARY OF THE INVENTION

The present invention relates to compounds of Formula 1

Formula 1

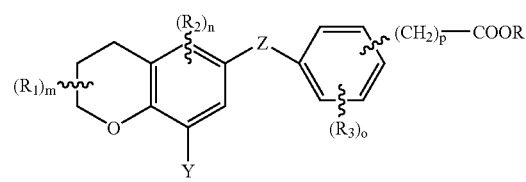

wherein Z is COO or C≡C;
 $R_1$ is alkyl having 1 to 6 carbons;
 $R_2$ is independently alkyl of 1 to 6 carbons, F, Cl, Br, I, $CF_3$, fluoro substituted alkyl of 1 to 6 carbons, OH, SH, alkoxy of 1 to 6 carbons or alkylthio of 1 to 6 carbons;
 $R_3$ is independently alkyl of 1 to 6 carbons, F, Cl, Br, I, $CF_3$, fluoro substituted alkyl of 1 to 6 carbons, OH, SH, alkoxy of 1 to 6 carbons or alkylthio of 1 to 6 carbons;
 m is an integer having the values of 0 to 6;
 n is an integer having the values of 0 to 2;
 o is an integer having the values of 0 to 4;
 p is an integer having the values 0, 1, or 2;
 Y is CH≡C—, CH≡C—$CH_2$—; $CH_2$=CH— or C≡N;
 R is is H, alkyl of 1 to 6 carbons, —$CH_2OR_4$, $CH_2$—O—$COR_4$, or a cation of a pharmaceutically acceptable base, and
 $R_4$ is alkyl having 1 to 6 carbons.

In a second aspect, this invention relates to the use of the compounds of Formula 1 for the prevention or treatment of diseases and conditions in mammals, including humans, which diseases or conditions are prevented, treated, ameliorated, or the onset of which is delayed by administration of retinoid compounds or by the mammalian organism's naturally occurring retinoic acid. Because the compounds act as inhibitors of the breakdown of retinoic acid, the invention also relates to the use of the compounds of Formula 1 in conjunction with retinoic acid or other retinoids, and particularly in conjunction with Vitamin A, or with derivatives of Vitamin A having vitamin A activity. In this regard it is noted that retinoids are useful for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The retinoids are also useful for the prevention and treatment of metabolic diseases such as type II non-insulin dependent diabetes mellitus (NIDDM) and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. Retinoids can also be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoids include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

This invention also relates to a pharmaceutical formulation comprising one or more compounds of Formula 1 in admixture with a pharmaceutically acceptable excipient, said formulation being adapted for administration to a mammal, including a human being, to treat or alleviate the conditions which were described above as treatable by retinoids, or which are controlled by or responsive to the organism's native retinoic acid. These formulations can also be co-administered with retinoids and/or Vitamin A to enhance or prolong the effects of medications containing retinoids, Vitamin A or of the organism's native retinoic acid.

The invention also relates to the methods of using these formulations to treat or alleviate the conditions which were described above as treatable by retinoids, or which are controlled by or responsive to the organism's native retinoic acid.

BRIEF DESCRIPTION OF THE DRAWING FIGURE

FIG. 1 is a schematic representation of the P450RAI cell based assay utilized to evaluate the ability of the compounds of the invention to inhibit the Cytochrome P450RAI enzyme.

BIOLOGICAL ACTIVITY MODES OF ADMINISTRATION

P450RAI-1 and P450RAI-2 Cell-Based Inhibitor Assay:

FIG. 1 shows a schematic diagram of the P450RAI-1 and P450RAI-2 cell based assay. P450RAI-1 stably transfected HeLa cells, or P450RAI-2 stably transfected HeLa cells, as applicable, are maintained in 100 millimolar tissue culture dishes in Modified Eagle's Medium (MEM) containing 10% Fetal Bovine Serum (FBS) and 100 µg/ml hygromycin. Exponentially growing cells are harvested by incubating in trypsin. Cells are then washed with 1X Phosphate Buffered Saline (PBS) and plated in a 48-well plate at $5 \times 10^5$ cells in 0.2 ml MEM medium containing 10% FBS and 0.05 µCi [$^3$H]-RA in the presence or absence of increasing concentrations of the test compounds. The compounds are diluted in 100% DMSO and then added in triplicate wells at either 10, 1 or 0.1 µM final concentration. As a positive control for RA metabolism inhibition, cells are also incubated with ketoconazole at 100, 10 and 1 µM. Cells are incubated for 3 hours at 37° C. The retinoids are then extracted using the procedure of Bligh et al. (1959) Canadian Journal of Biochemistry 37, 911-917, modified by using methylenechloride instead of chloroform. The publication Bligh et al. (1959) Canadian Journal of Biochemistry 37, 911-917 is specifically incorporated herein by reference. The water soluble radioactivity is quantified using a β-scintillation counter. $IC_{50}$ values represent the concentration of inhibitor required to inhibit all-trans-RA metabolism by 50 percent and are derived manually from log-transformed data. The $IC_{50}$ values obtained in this assay for several preferred compounds of the invention with both the RAI-1 and RAI-2 enzymes are disclosed in Table 1 below.

Assays of Retinoid-like or Retinoid Antagonist and Inverse Agonist-like Biological Activity Assays described below measure the ability of a compound to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$ and $RXR_\gamma$ receptors, and the ability or inability of the compounds to activate transcription of a reporter gene through these receptor subtypes can be tested.

As far as specific assays are concerned, a chimeric receptor transactivation assay which tests for agonist-like activity in the $RAR_\alpha$, $RAR_\beta$, and $RAR_\gamma$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference. The numeric results obtained with several preferred compounds of this invention in this assay are shown below in Table 1. These data demonstrate that generally speaking the compounds are not agonists (or only weak agonists) of RAR retinoic receptors, and also that they do not bind, or in some cases bind only weakly to RAR retinoid receptors.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30-33 and 37-41) published on Jun. 24, 1993, the specification of which is also incorporated herein by reference. A detailed experimental procedure for holoreceptor transactivations has been described by Heyman et al. Cell 68, 397-406, (1992); Allegretto et al. J. Biol. Chem. 268, 26625-26633, and Mangelsdorf et al. The Retinoids: Biology, Chemistry and Medicine, pp 319-349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et al. Biochemical Pharmacology Vol. 22 pp 3099-3108, expressly incorporated herein by reference.)

The results of the ligand binding assay for several preferred compounds of the invention are included in Table 1. In the holoreceptor transactivation assay, tested for $RXR_\alpha$, $RXR_\beta$, and $RXR_\gamma$ receptors, the compounds of the present invention are, generally speaking, entirely devoid of activity, demonstrating that the compounds of the invention do not act as RXR agonists.

TABLE 1

| Compound | | RAR $EC_{50}$/(EFFICACY)/$K_d$ nM | | | P450RAI INHIBITION DATA | |
|---|---|---|---|---|---|---|
| | | | | | RAI-1 Intact cells | RAI-2 Intact Cells |
| No. | STRUCTURE | α | β | γ | $IC_{50}$ μM | $IC_{50}$ μM |
| 1 | 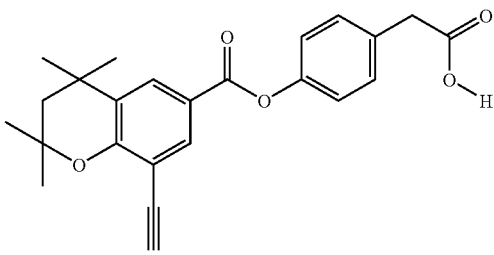 | $NA^1$ >10 K | $WA^2$ (15) >10 K | NA >10 K | 0.5 | 0.014 |
| 2 | 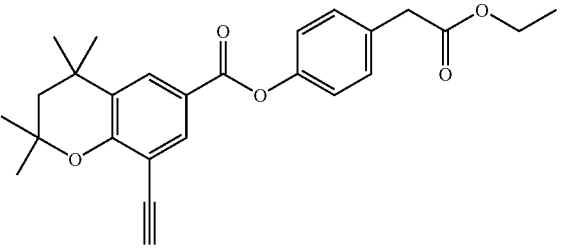 | NA >10 K | WA >10 K | NA >10 K | 6 | 6 |
| 3 | 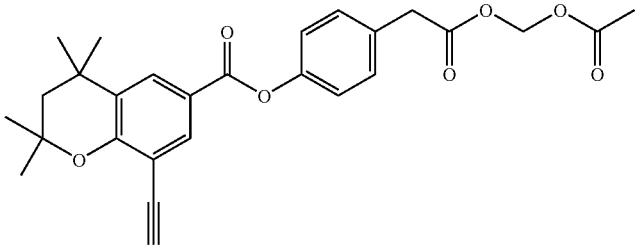 | NA >10 K | WA >10 K | NA >10 K | 0.5 | 0.08 |

TABLE 1-continued

| Compound No. | STRUCTURE | RAR $EC_{50}$/(EFFICACY)/$K_d$ nM | | | P450RAI INHIBITION DATA | |
|---|---|---|---|---|---|---|
| | | | | | RAI-1 Intact cells | RAI-2 Intact Cells |
| | | α | β | γ | $IC_{50}$ μM | $IC_{50}$ μM |
| 4 | 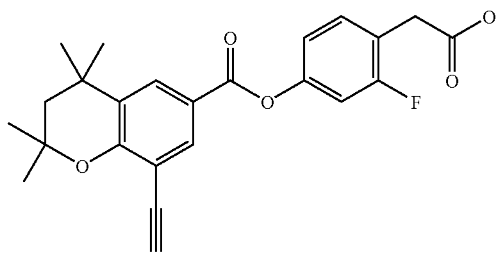 | WA (20) 3474 | 263 (78) 6562 | WA (20) >10 K | 0.1 | 0.06 |
| 5 | 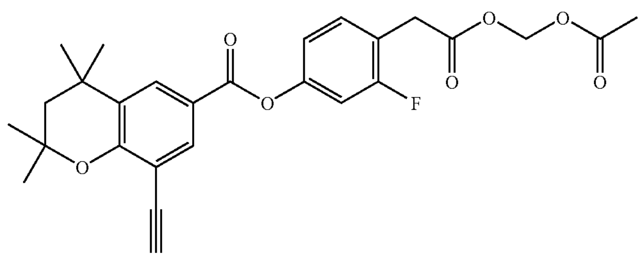 | WA (10) 4684 | WA (40) 5548 | NA >10 K | 0.075 | 0.03 |
| 40 | 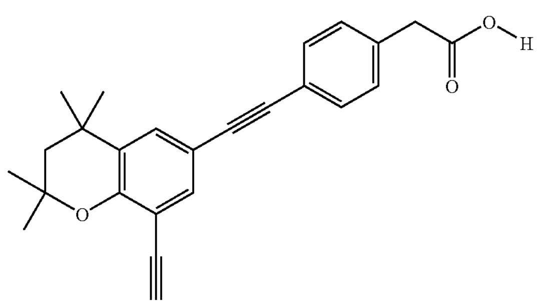 | 129 (15) >10 K | 101 (48) 7621 | 149 (30) >10 K | 0.01 | 0.007 |
| 41 | 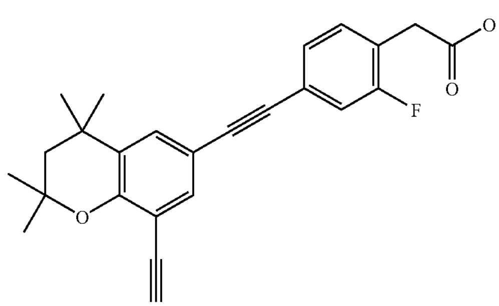 | WA (10) >10 K | WA (40) 4948 | WA (20) >10 K | 0.004 | 0.004 |
| 49 | 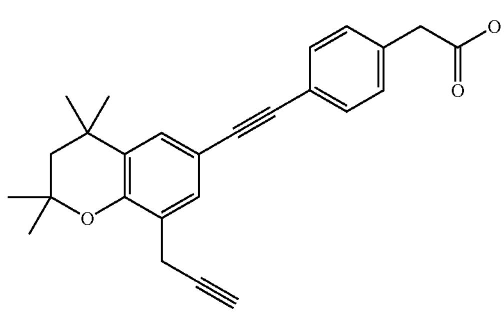 | NA 7244 | WA (20) >10 K | NA 8239 | 0.018 | 0.12 |

TABLE 1-continued

| Compound No. | STRUCTURE | RAR EC$_{50}$/(EFFICACY)/K$_d$ nM | | | P450RAI INHIBITION DATA | |
|---|---|---|---|---|---|---|
| | | α | β | γ | RAI-1 Intact cells IC$_{50}$ μM | RAI-2 Intact Cells IC$_{50}$ μM |
| 32 | 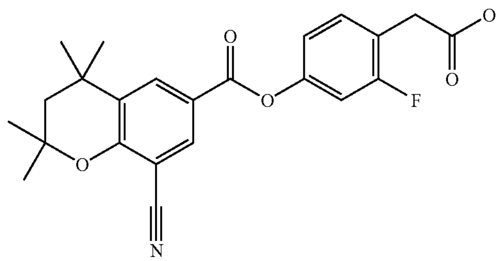 | NA >10 K | NA (15) >10 K | NA >10 K | 0.1 | 0.9 |
| 33 | 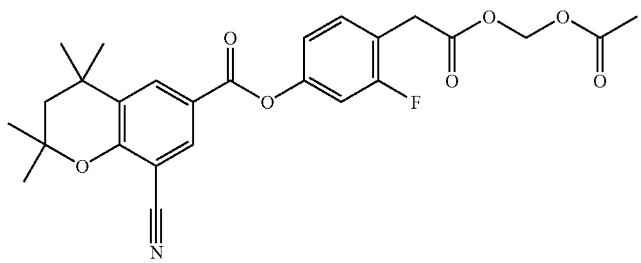 | NA >10 K | NA (10) >10 K | NA >10 K | 0.1 | 0.7 |

NA[1] = Not Active; WA[2] = Weakly Active

Topical Skin Irritation Tests

The topical retinoid all-trans-retinoic acid (ATRA) and oral retinoids such as 13-cis RA and etretinate are known to induce substantial skin irritation in humans. This irritation is a direct result of activation of the RAR nuclear receptors. Analysis of retinoid topical irritation is also a highly reproducable method of determining in vivo retinoid potency. The female fuzzy rats provide a convenient animal model of topical irritation, since retinoid-induced skin flaking and abrasion can be readily scored by eye, while their larger size than those of mice also allows multiple sampling of serum for clinical analyses. Topical application of P450RAI inhibitors should cause an increase in the endogenous levels of ATRA that would result in ATRA-induced irritation in skin of hairless mice.

In these tests female fuzzy rats ((Hsd:FUZZY-fz), 6-7 weeks old, were obtained from Harlan Sprague-Dawley (Indianapolis, Ind.). The animals were about 8-9 weeks old at the start of the experiments. Food (Purina Rodent Chow 5001) and water purified by reverse osmosis were provided ad libitum. The rats were housed individually throughout the dosing period. Test chemicals were dissolved in acetone (vehicle) for application to the backs of the rats. Two days prior to actual administration of the test compounds, rats were handled daily and dosed with vehicle at a volume of 0.5 ml/kg. Starting on Day 1 thought Day 14 (dosing period), animals were dosed with the vehicle or compound(s) according to their group assignment.

The rats in the tests were observed daily and the dorsal skin was graded for the degree of erythema/eschar and overall appearance. The scoring was in accordance with Table 2, below.

TABLE 2

| Grade | Erythema and Eschar Formation |
|---|---|
| 0 | No erythema. |
| 1 | Very slight erythema (barely perceptible redness). |
| 2 | Well-defined erythema (mild-clear visible redness). |
| 3 | Moderate to severe erythema (prominent redness). |
| 4 | Severe erythema (dark redness) to slight eschar formation (loss of epidermal cells or sloughing). The present of fissures, abrasions, erosion, and/or ulceration may be used in the evaluation of the severity of erythema. |

Daily group average was calculated by dividing the sum of the individual grade by the number of animals in each treatment group.

The attached data in Table 3 indicates the retinoid-mimetic effects of some P450RAI inhibitors on the skin of fuzzy rats in the above described tests and in accordance with the above-indicated scoring.

TABLE 3

| Compound # | Irritation Score on day 14 |
|---|---|
| 0.1% retinol (Vitamin A) | 1 |
| 0.1 retinol + 1% Compound 4 | 3.4 |
| 1% Compound 4 | 1.4 |

TABLE 3-continued

| Compound # | Irritation Score on day 14 |
|---|---|
| 0.1% retinol + 1% Compound 3 | 2.4 |
| 1% Compound 3 | 0 |
| 0.1% retinol + 1% Compound 2 | 1.6 |
| 1% Compound 2 | 0 |
| 0.1% retinol + 0.1% Compound 5 | 2.2 |
| 0.1% Compound 5 | 0.4 |
| 0.1% retinol + 3% Compound 1 | 1 |
| 3% Compound 1 | 2.6 |

Modes of Administration

The compounds of this invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds, or to control by naturally occurring retinoic acid will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg of body weight per day would be expected to effect a therapeutic result in the treatment of many diseases for which these compounds are useful.

In some applications pharmaceutical formulations containing the CP-450RAI inhibitory compounds of the invention may be co-administered with formulations containing retinoids. In some other important applications the pharmaceutical formulations containing the CP-450RAI inhibitory compounds of the invention may be co-administered with Vitamin A.

General Embodiments

Definitions

The term alkyl refers to and covers any and all groups which are known as normal alkyl and branched-chain alkyl. Unless specified otherwise, where the term lower alkyl is used it means the above-defined broad definition of alkyl groups having 1 to 6 carbons in case of normal lower alkyl, and 3 to 6 carbons for lower branch chained alkyl groups.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Some of the compounds of the present invention may contain one or more chiral centers and therefore may exist in enantiomeric and diastereomeric forms. The scope of the present invention is intended to cover all isomers per se, mixtures of diastereomers and racemic mixtures of enantiomers (optical isomers) as well.

Specific Embodiments

With reference to the variable $R_1$ of Formula 1 the preferred compounds of the invention are those where this variable represents methyl groups. Even more preferably the methyl or other alkyl groups represented by the $R_1$ variable are located in the 2 and 4 positions of the chroman ring.

With reference to the variable $R_2$ of Formula 1 the presently preferred compounds of the invention are those where the aromatic portion of the chroman ring is unsubstituted except by the Y group in the 8 position and by the carbonyloxy-phenyl or ethynyl groups in the 6 position. Accordingly in the most preferred compounds of the invention the variable n is zero. In alternative preferred compounds of the invention n is 1 or 2, and $R_2$ is alkyl or halogen.

The phenyl group of the preferred compounds of the invention is preferably 1,4 (para) substituted by the $(CH_2)_p COOR$ and 6-chromanoyl or by the chroman-6-yl-ethynyl groups. In the most preferred compounds of the invention the phenyl group either has no substituent other than the above-mentioned $(CH_2)_p COOR$ and 6-chromanoyl or chroman-6-yl-ethynyl groups (the variable o is zero) or the phenyl group has one halogen, preferably fluoro substituent ($R_3$=F and o is 1) and the fluoro substituent is preferably in the 1,2 (ortho) position relative to the $(CH_2)_p COOR$. Compounds where the $R_3$ group is alkyl are also preferred.

Still with reference to Formula 1 in the preferred compounds of the invention the variable Y represents an ethynyl (CH≡C—) group, a cyano group or an ethynylmethyl group. The preferred compounds of the invention are phenylacetic acid derivatives so that the preferred value for the variable p is 1.

The most preferred compounds of the invention are shown below by specific formulas

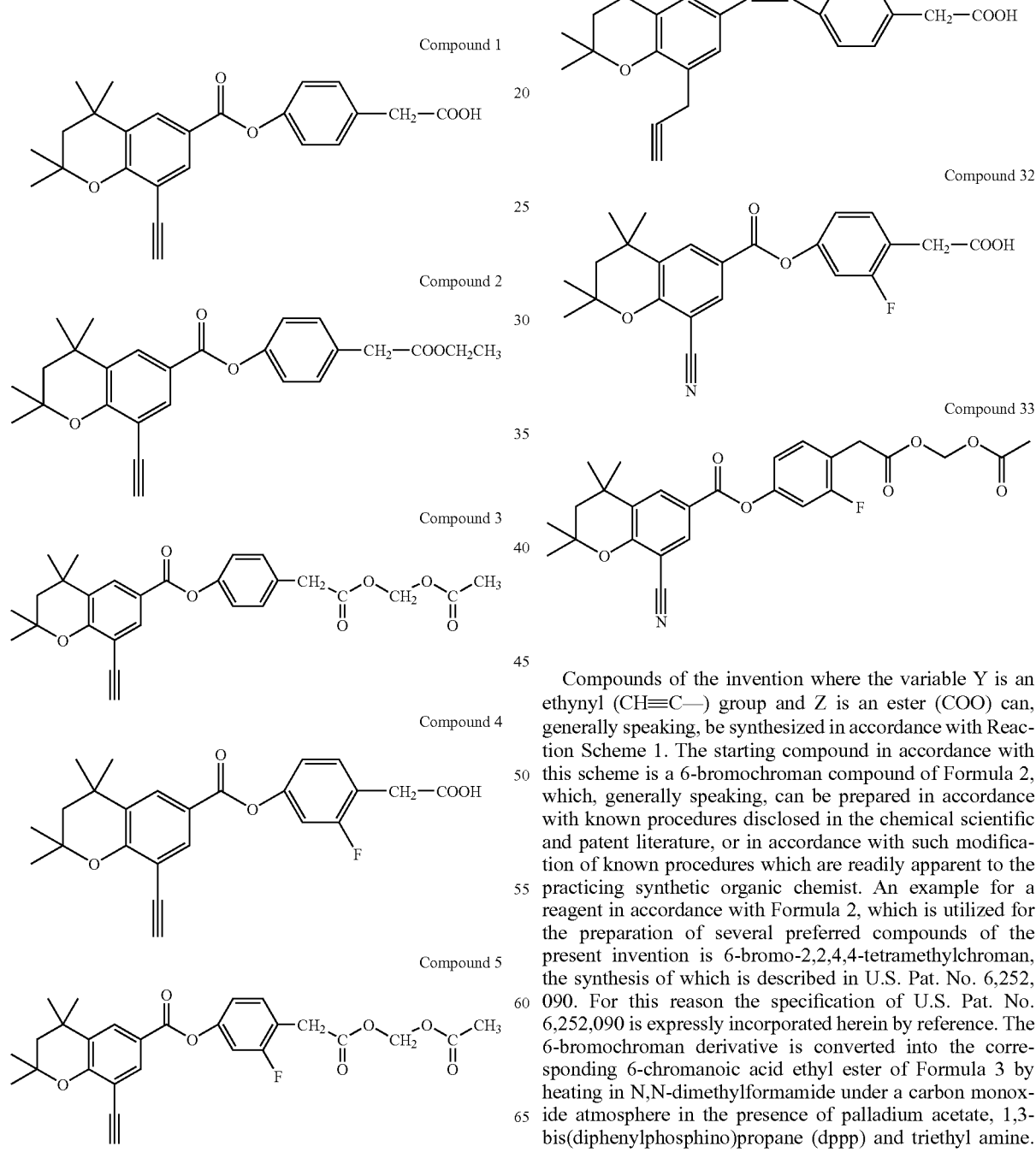

Compounds of the invention where the variable Y is an ethynyl (CH≡C—) group and Z is an ester (COO) can, generally speaking, be synthesized in accordance with Reaction Scheme 1. The starting compound in accordance with this scheme is a 6-bromochroman compound of Formula 2, which, generally speaking, can be prepared in accordance with known procedures disclosed in the chemical scientific and patent literature, or in accordance with such modification of known procedures which are readily apparent to the practicing synthetic organic chemist. An example for a reagent in accordance with Formula 2, which is utilized for the preparation of several preferred compounds of the present invention is 6-bromo-2,2,4,4-tetramethylchroman, the synthesis of which is described in U.S. Pat. No. 6,252,090. For this reason the specification of U.S. Pat. No. 6,252,090 is expressly incorporated herein by reference. The 6-bromochroman derivative is converted into the corresponding 6-chromanoic acid ethyl ester of Formula 3 by heating in N,N-dimethylformamide under a carbon monoxide atmosphere in the presence of palladium acetate, 1,3-bis(diphenylphosphino)propane (dpp) and triethyl amine. The 6-chromanoic acid ethyl ester of Formula 3 is thereafter treated with silver(I) trifluoromethanesulfonate and iodine to provide the 8-iodo-6-chromanoic acid ethyl ester derivative of Formula 4. The iodo compound of Formula 4 is reacted with trimethylsilyl acetylene in triethyl amine under argon atmosphere in the presence of copper(I)iodide and dichlorobis(triphenylphosphine)palladium(II) (Pd(PPh$_3$)$_2$Cl$_2$). The trimethylsilyl group and the ethyl group of the ester moiety of the resulting 8-trimethylsilyl 6-chromanoic acid ethyl ester of Formula 5 are then removed by treatment with base (such as sodium hydroxide shown in the reaction scheme) to provide the 8-ethynyl-6-chromanoic acid of Formula 6.

REACTION SCHEME 1

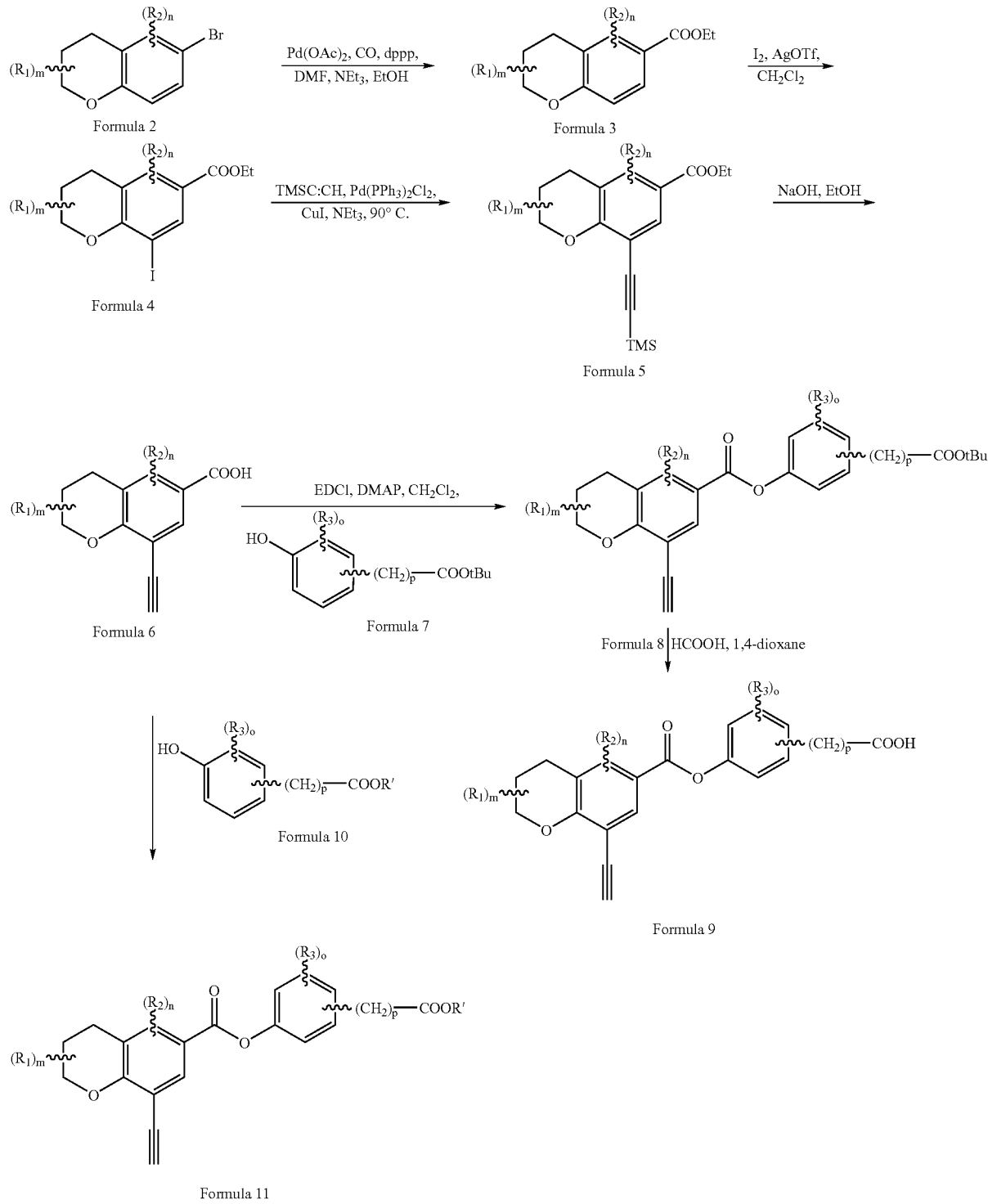

The 8-ethynyl-6-chromanoic acid of Formula 6 is then coupled with a hydroxy-benzoic acid ester, hydroxy-phenylacetic acid ester, or with a hydroxy-phenyl propanoic acid ester compound of Formula 7 or of Formula 10 in an esterification reaction to provide compounds of Formula 8 or Formula 11. The esterification reaction can be conducted in accordance with methods known in the state of the art, the presently preferred method shown in Reaction Scheme 1 is reaction of the free 6-chromanoic acid derivative of Formula 6 with the hydroxyphenyl compound of Formula 7 or of Formula 10 in an anhydrous solvent (such as methylene chloride) in the presence of a water acceptor such as 1-(3-dimethylaminopropyl)-3-ethylcarbodiimide hydrochloride (EDCI) and an acid acceptor such as 4-(dimethylamino)pyridine (DMAP). The hydroxy-benzoic acid ester, hydroxy-phenylacetic acid ester, or hydroxy-phenyl propanoic acid ester compounds of Formula 7 or of Formula 10, generally speaking, can be prepared in accordance with known procedures disclosed in the chemical scientific and patent literature, or in accordance with such modification of known procedures which are readily apparent to the practicing synthetic organic chemist. Nevertheless, the synthesis of specific examples of compounds of Formula 7 and of Formula 10 are provided below, because these specific compounds are used for the synthesis of several preferred compounds of the invention.

The compounds of Formula 7 are tertiary-butyl esters and therefore in the reaction with the 8-ethynyl-chromanoic acids of Formula 6 they yield tertiary-butyl esters of Formula 8. The tertiary-butyl esters of Formula 8 are themselves within the scope of the invention, but are usually converted into the more preferred free acid compounds of Formula 9 by treatment with acid (such as formic acid) in an anhydrous aprotic solvent, such as dioxane. The synthetic process utilizing the tertiary-butyl ester intermediate of Formula 8 is preferred when the ultimate objective is to obtain a compound of the invention having a free carboxylic acid group, or its pharmaceutically acceptable salt.

The compounds of Formula 10 are other esters of hydroxy-benzoic acid, hydroxy-phenylacetic acid, or of hydroxy-phenyl propanoic acid where the variable R' is defined as in connection with Formula 1 except that R' is not hydrogen. The synthetic process utilizing the ester intermediates of Formula 10 is preferred when the ultimate objective is to obtain a compound of the invention having an esterified carboxylic group in the benzoic, phenylacetic acid or phenyl propanoic acid moiety. As it was noted above phenylacetic acid moieties are generally preferred in the present invention.

Reaction Schemes 2, 3, 4, 5 and 6 disclose the presently preferred synthetic processes for obtaining specific examples of those compounds in accordance with Formula 7 and Formula 10 which are utilized for the synthesis of the presently preferred examples of the invention. A detailed description of the reagents and reactions utilized in these synthetic routes is provided in the experimental section of the application. A detailed description of the synthesis of Compound 6 shown in Reaction Scheme 2 is described in U.S. Pat. No. 6,252,090, incorporated herein by reference.

Reaction Schemes 7, 8, 9, 10 and 11 disclose the presently preferred synthetic processes for obtaining the preferred exemplary compounds of the invention where the variable Z is an ester (COO) and the variable Y is ethynyl. A detailed description of the reagents and reactions utilized in these synthetic routes is provided in the experimental section.

REACTION SCHEME 2

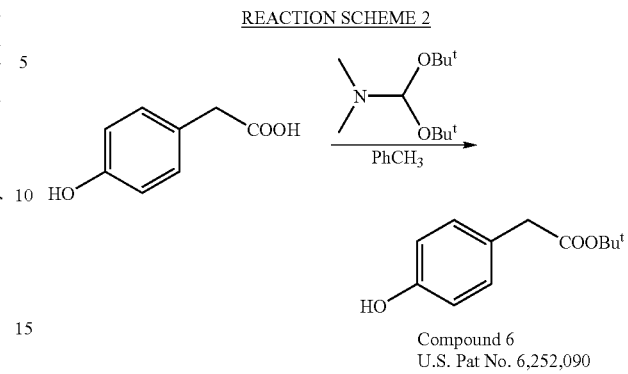

Compound 6
U.S. Pat No. 6,252,090

REACTION SCHEME 3

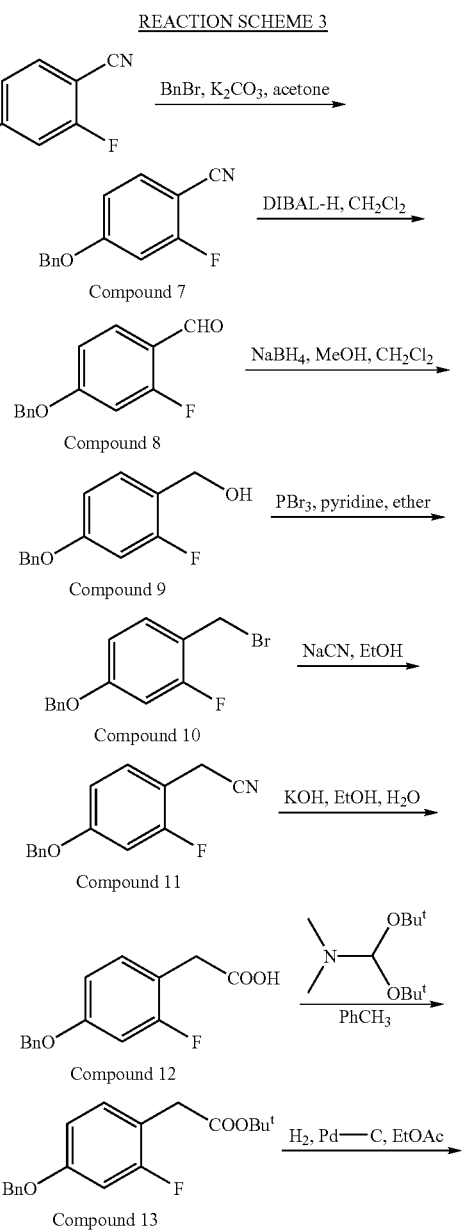

-continued
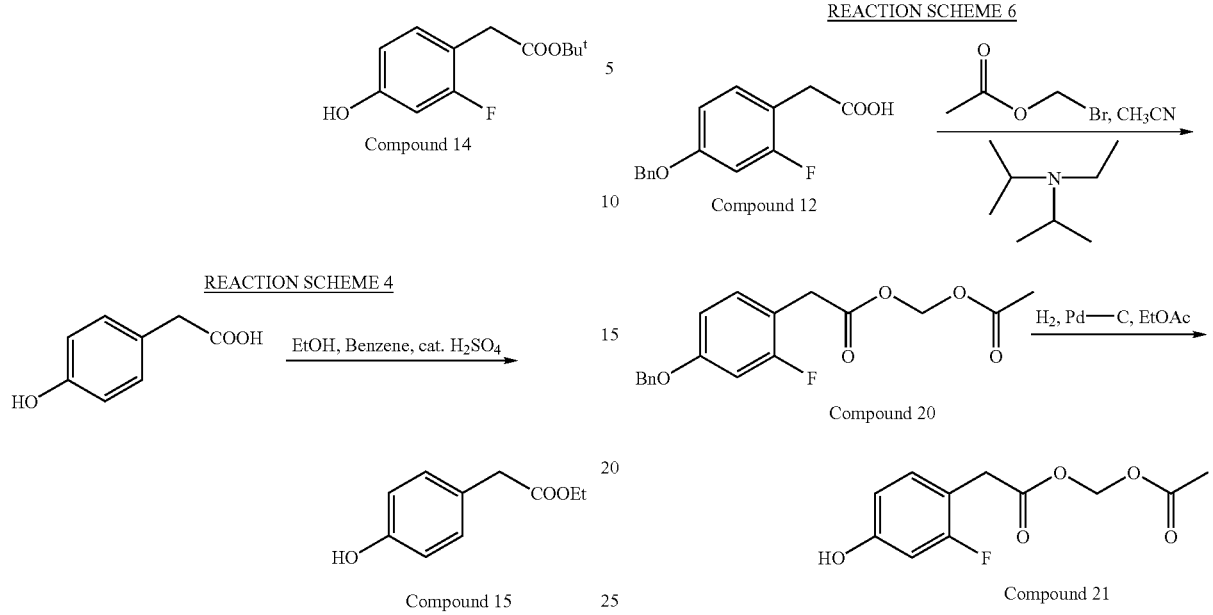
REACTION SCHEME 4
REACTION SCHEME 5
REACTION SCHEME 6
REACTION SCHEME 7
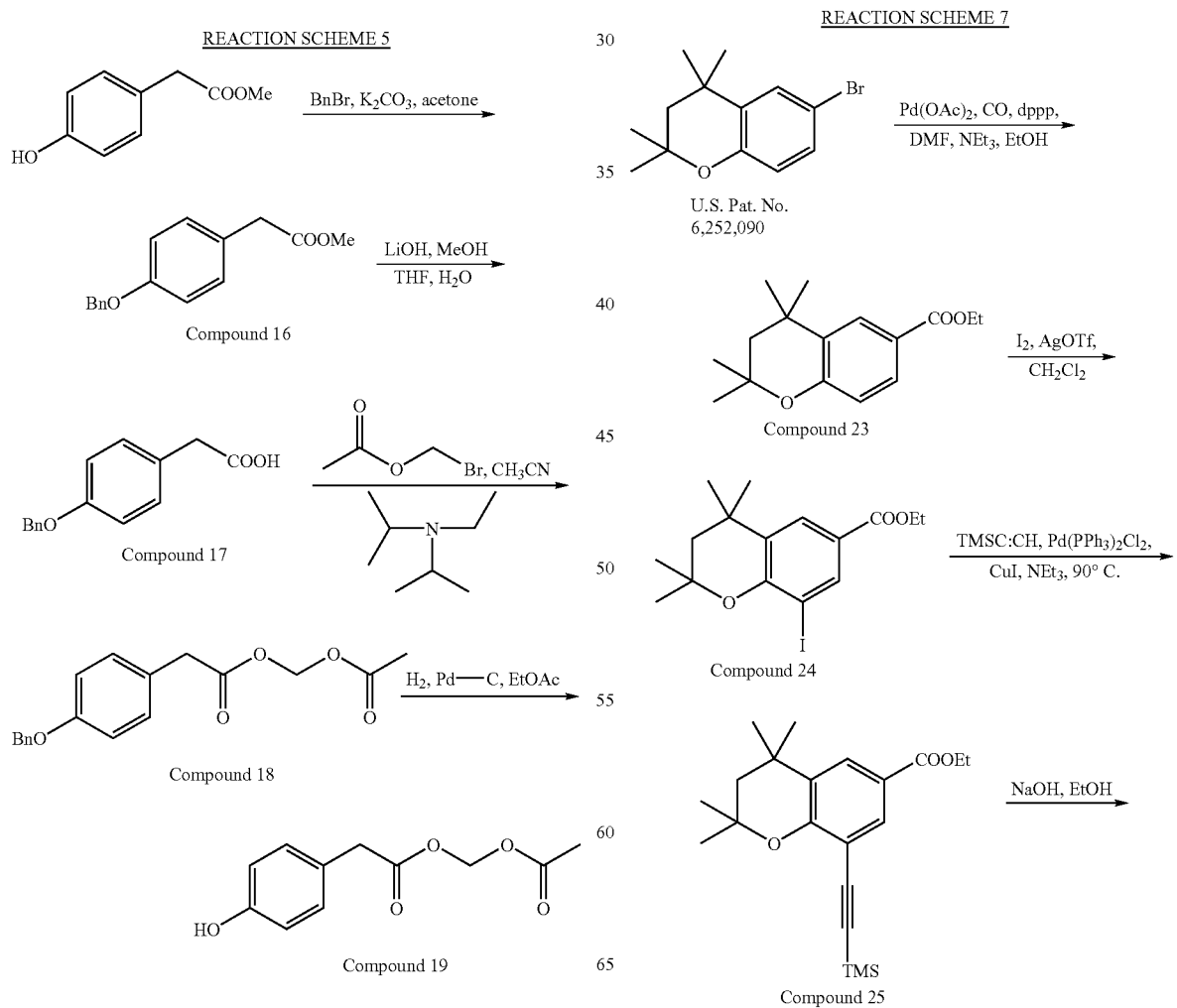

-continued
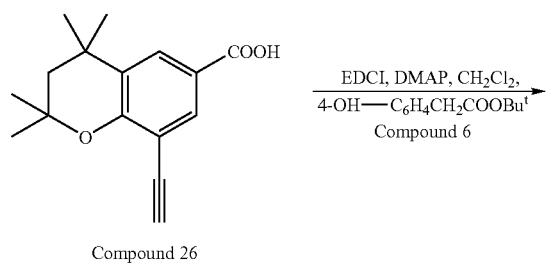
Compound 26
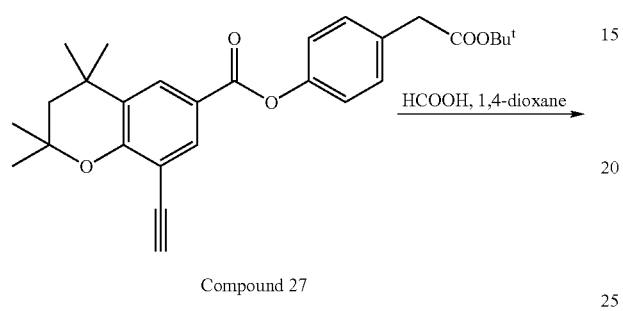
Compound 27
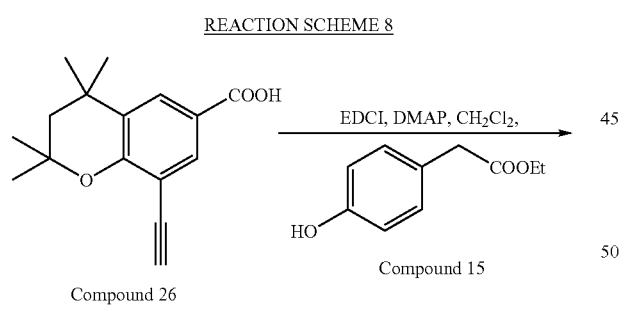
Compound 1
REACTION SCHEME 8
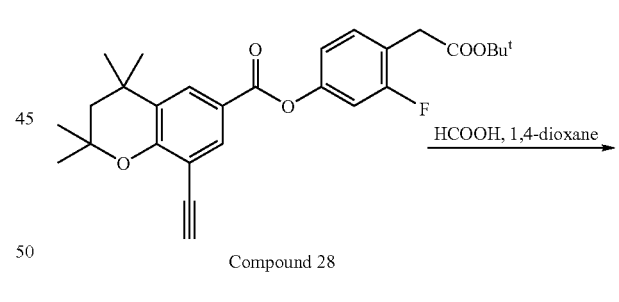
Compound 2
REACTION SCHEME 9
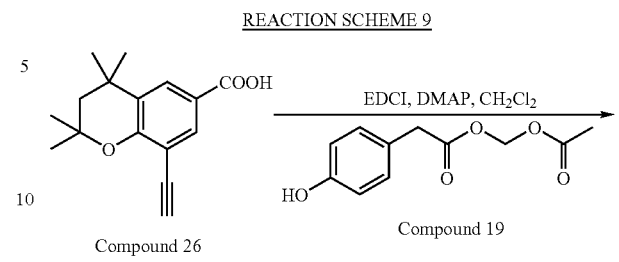
Compound 26
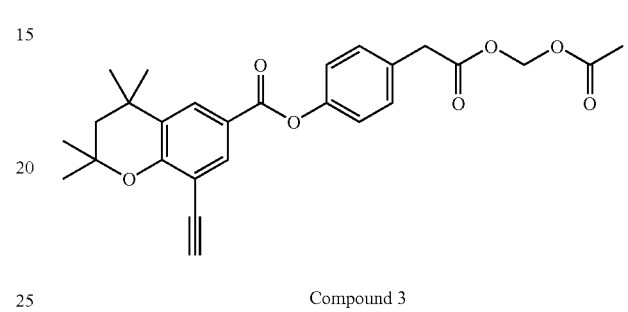
Compound 3
REACTION SCHEME 10
Compound 26
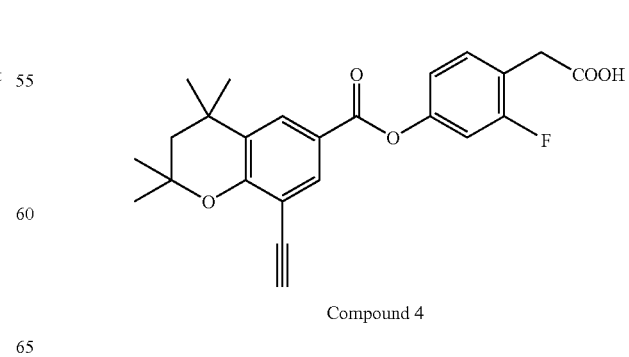
Compound 28
Compound 4

REACTION SCHEME 11

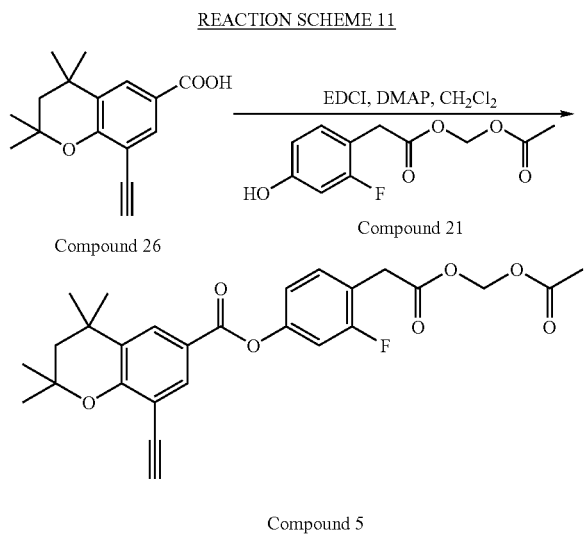

Compound 26

Compound 21

Compound 5

Compounds of the invention where the variable Y is an ethynyl-methyl (CH≡C—CH$_2$—) group can, generally speaking, be synthesized in accordance with Reaction Scheme 12. The starting compound in accordance with this scheme is a 6-chromanoic acid ethyl ester derivative of Formula 3 which can be obtained as described above in connection with Reaction Scheme 1. The 6-chromanoic acid ethyl ester of Formula 3 is thereafter treated with α,α-dichloromethyl methyl ether in a suitable aprotic solvent such as methylene chloride to provide the 8-formyl-6-chromanoic acid ethyl ester derivative of Formula 12. The formyl compound of Formula 12 is reduced with sodium borohydride in methanol to give the corresponding hydroxymethyl compound of Formula 13. The hydroxymethyl compound of Formula 13 is then reacted with N-bromosuccinimide in the presence of triphenylphosphine in an aprotic solvent such as methylene chloride to give the 8-(bromomethyl)-6-chromanoic ester derivative of Formula 14. The 8-(bromomethyl)-6-chromanoic ester derivative of Formula 14 is reacted with trimethylsilyl acetylene in triethyl amine and dimethylformamide (DMF) under argon atmosphere in the presence of dichlorobis(triphenylphosphine)palladium(II) (Pd(PPh$_3$)$_2$Cl$_2$). The trimethylsilyl group and the ethyl group of the ester moiety of the resulting 8-(trimethylsilylmethyl) 6-chromanoic acid ethyl ester are then removed by treatment with base (such as lithium hydroxide shown in the reaction scheme) to provide the 8-(ethynylmethyl)-6-chromanoic acid of Formula 15.

The (8-ethynylmethyl)-6-chromanoic acid of Formula 15 is then coupled with a hydroxy-benzoic acid ester, hydroxy-phenylacetic acid ester, or with a hydroxy-phenyl propanoic acid ester compound of Formula 7 or of Formula 10 in an esterification reaction to provide compounds of Formula 16 or Formula 18. The esterification reaction can be conducted in accordance with methods known in the state of the art, as is described in connection with Reaction Scheme 1. In this synthetic route also, the preferred method of esterification is the reaction of the free 6-chromanoic acid derivative of Formula 15 with the hydroxyphenyl compound of Formula 7 or of Formula 10 in an anhydrous solvent (such as methylene chloride) in the presence of a water acceptor such as 1-(3-dimethylaminopropyl)-3-ethylcarbodiimide hydrochloride (EDCI) and an acid acceptor such as 4-(dimethylamino)pyridine (DMAP). The hydroxy-benzoic acid ester, hydroxy-phenylacetic acid ester, or hydroxy-phenyl propanoic acid ester compounds of Formula 7 or of Formula 10, generally speaking, can be prepared as described in connection with Reaction Scheme 1.

The compounds of Formula 7 are tertiary-butyl esters and therefore in the reaction with the 8-(ethynylmethyl)-chromanoic acids of Formula 15 they yield tertiary-butyl esters of Formula 16. The tertiary-butyl esters of Formula 16 are themselves within the scope of the invention, but are usually converted into the more preferred free acid compounds of Formula 17 by treatment with acid (such as formic acid) in an anhydrous aprotic solvent, such as dioxane. The synthetic process utilizing the tertiary-butyl ester intermediate of Formula 16 is preferred when the ultimate objective is to obtain a compound of the invention having a free carboxylic acid group, or its pharmaceutically acceptable salt.

The compounds of Formula 10 are other esters of hydroxy-benzoic acid, hydroxy-phenylacetic acid, or of hydroxy-phenyl propanoic acid where the variable R' is defined as in connection with Formula 1 except that R' is not hydrogen. The synthetic process utilizing the ester intermediates of Formula 10 is preferred when the ultimate objective is to obtain a compound of the invention of Formula 18, having an esterified carboxylic group in the benzoic, phenylacetic acid or phenyl propanoic acid moiety. As it was noted above phenylacetic acid moieties are generally preferred in the present invention.

Compounds of the invention where the variable Y is a vinyl (CH$_2$=CH—) group can, generally speaking, be synthesized in accordance with Reaction Scheme 13. The starting compound in accordance with this scheme is an 8-formyl-6-chromanoic acid ethyl ester derivative of Formula 12 which can be obtained as described above in connection with Reaction Scheme 12. The 8-formyl-6-chromanoic acid ethyl ester of Formula 12 is thereafter treated with a Wittig reagent to provide an 8-vinyl-6-chromanoic acid ethyl ester derivative of Formula 19. The vinyl ester of Formula 19 is then treated with base to yield an 8-vinyl-6-chromanoic acid derivative of Formula 20. This free acid is coupled with a hydroxy-benzoic acid ester, hydroxy-phenylacetic acid ester, or with a hydroxy-phenyl propanoic acid ester compound of Formula 7 or of Formula 10 in an esterification reaction to provide compounds of Formula 21 or Formula 22 as is decribed above in connection with Reaction Schemes 1 and 12. The tertiary-butyl esters of Formula 21 are themselves within the scope of the invention, but are usually converted into the more preferred free acid compounds of Formula 23 by treatment with acid (such as formic acid) in an anhydrous aprotic solvent, such as dioxane. The compounds of Formula 22 are other esters of hydroxy-benzoic acid, hydroxy-phenylacetic acid, or of hydroxy-phenyl propanoic acid where the variable R' is defined as in connection with Formula 1 except that R' is not hydrogen. The synthetic process utilizing the ester intermediates of Formula 10 is preferred when the ultimate objective is to obtain a compound of the invention of Formula 22, having an esterified carboxylic group in the benzoic, phenylacetic acid or phenyl propanoic acid moiety. As it was noted above phenylacetic acid moieties are generally preferred in the present invention.

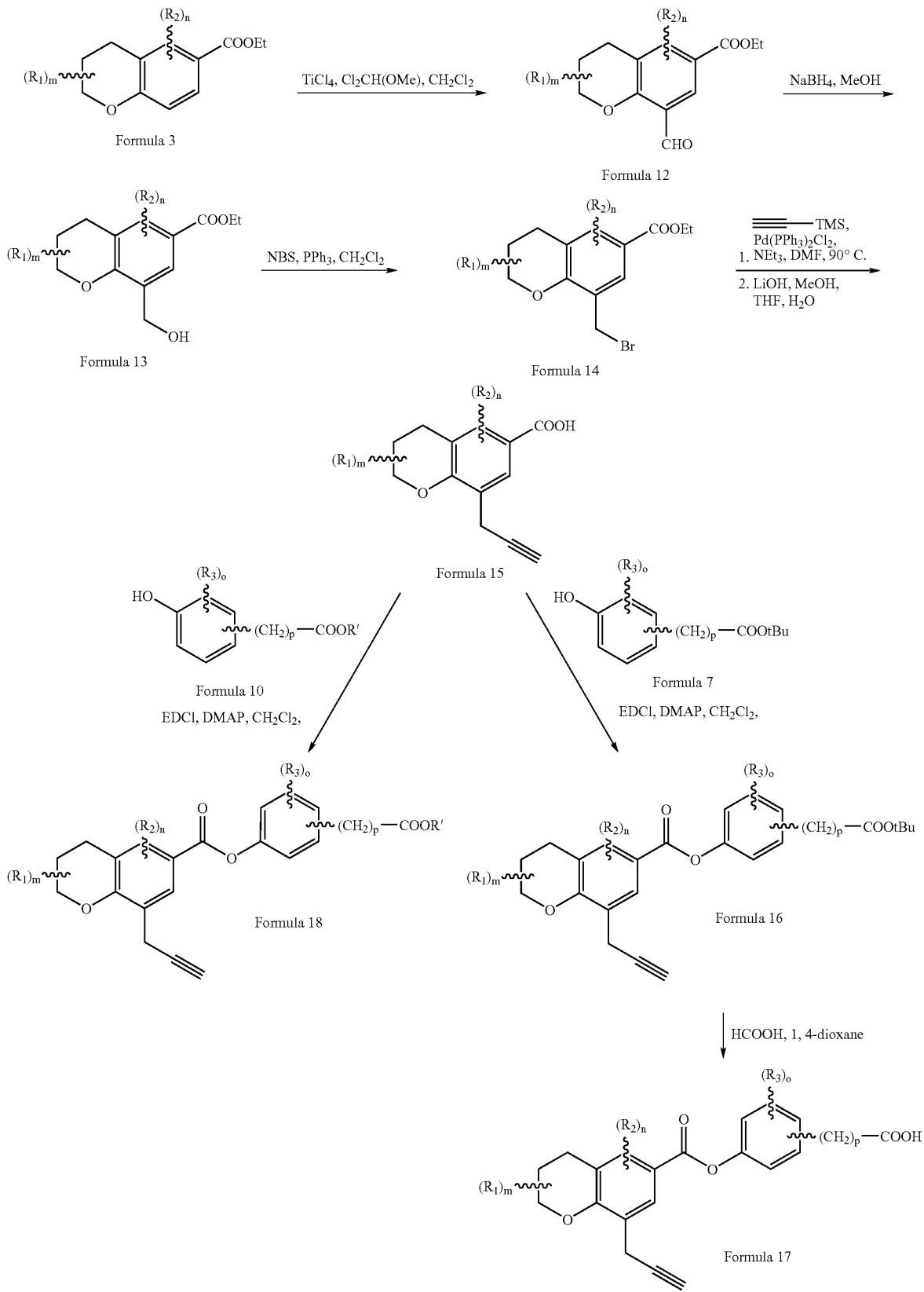

REACTION SCHEME 13
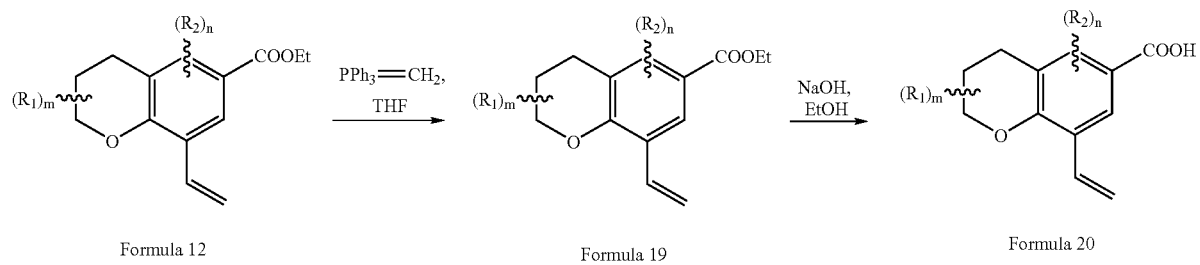
Formula 12 → Formula 19 → Formula 20
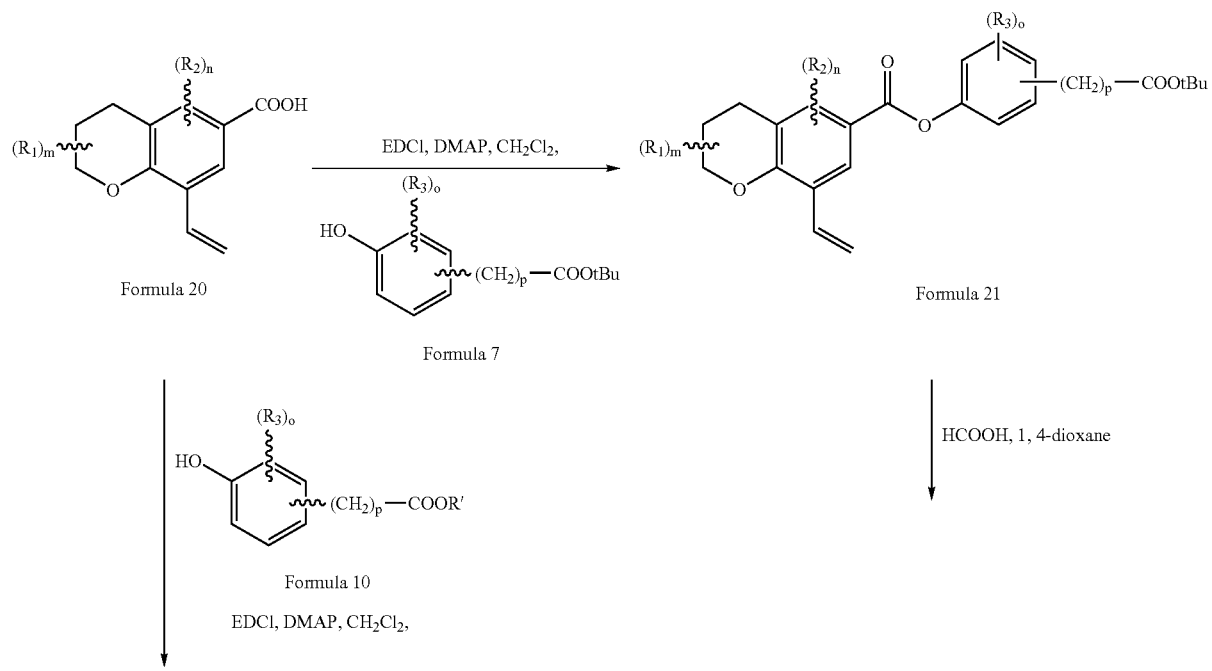
Formula 20 + Formula 7 → Formula 21
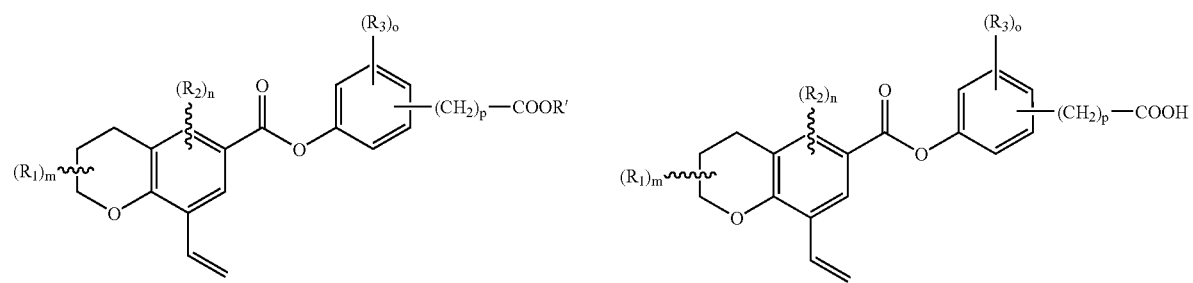
Formula 22    Formula 23

Compounds of the invention where the variable Y is a cyano (CN) group and the variable Z is COO can, generally speaking, be synthesized in accordance with Reaction Scheme 14, where the variables $R_1$, $R_2$, $R_3$, m, n and p are defined as in connection with Formula 1.

REACTION SCHEME 14

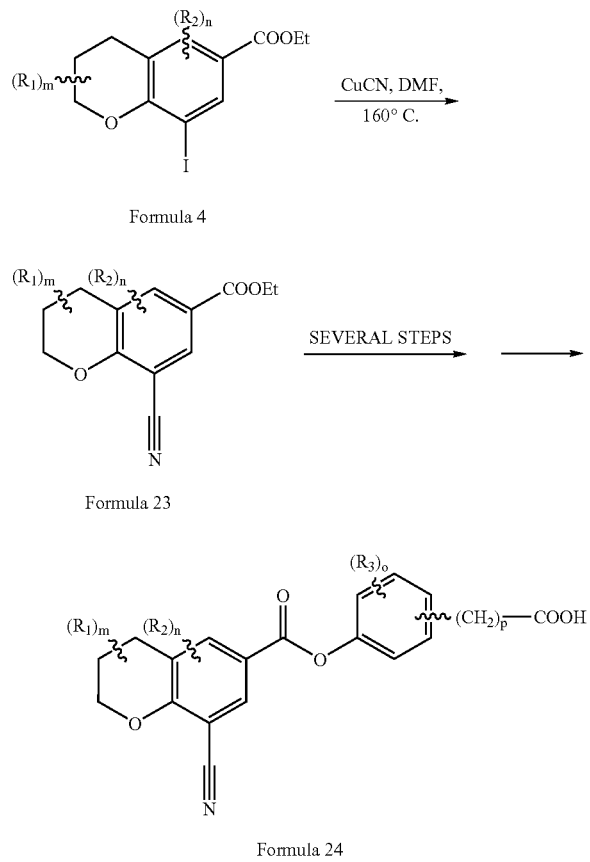

In Reaction Scheme 14 the starting material is a compound of Formula 4 that can be obtained as shown in Reaction Scheme 1. The compound of Formula 4 is heated with cuprous cyanide (CuCN) in dimethylformamide (DMF) to provide an 8-cyano-chroman-6-carboxylic acid ester derivative of Formula 23. The compound of Formula 23 is converted into 4-[(8-cyano)-6-chromanoyl]-benzoic and phenylacetic acids in reaction steps analogous to the steps described in Reaction Scheme 1. The 4-[(8-cyano)-6-chromanoyl]—benzoic and phenylacetic acids are within the scope of the invention and of Formula 1.

Reaction Scheme 15 discloses a general synthetic route to compounds of the invention where the variables Y and Z both represent ethynyl groups.

REACTION SCHEME 15

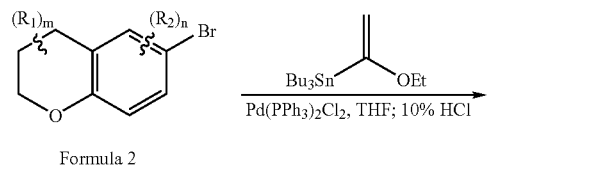

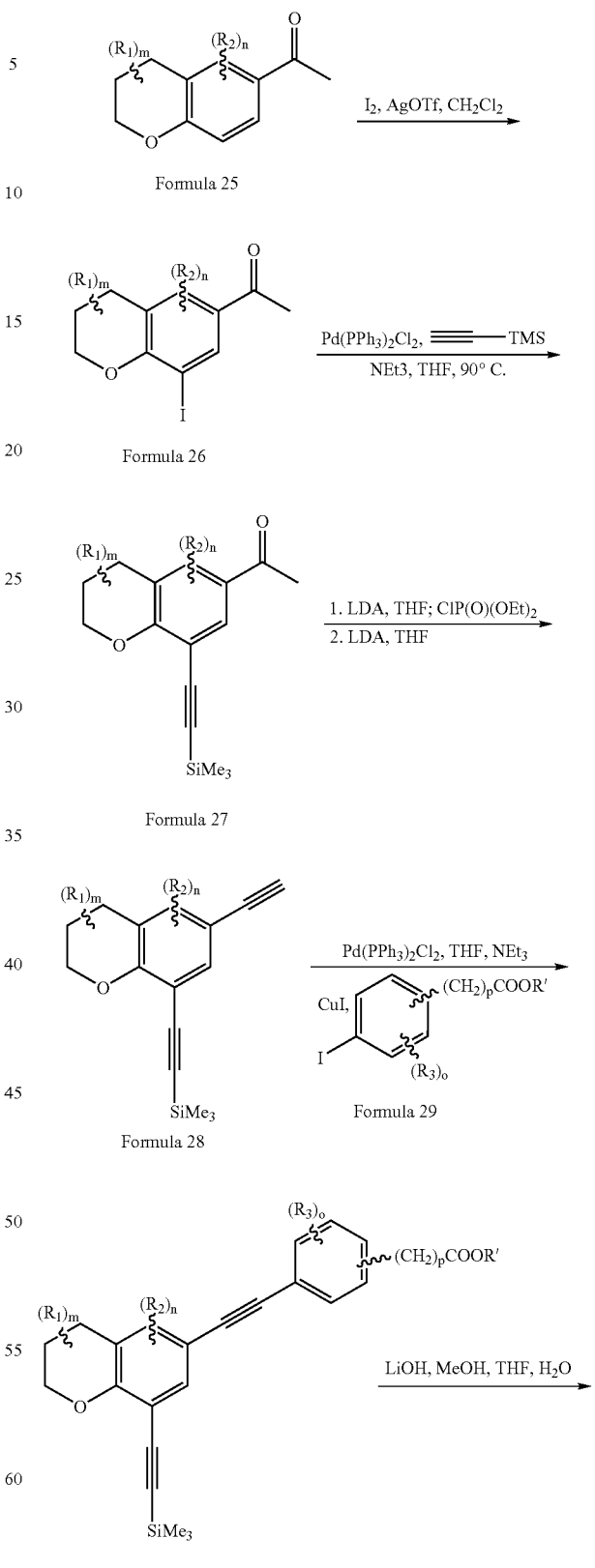

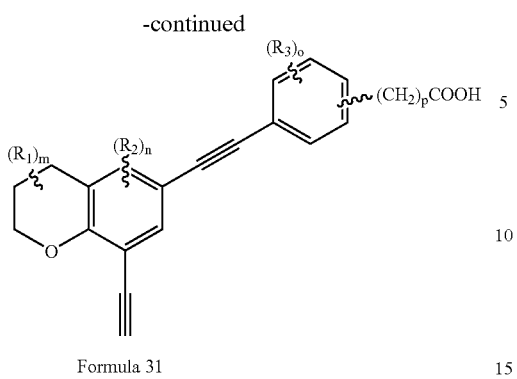

Formula 31

In accordance with this scheme a 6-bromochroman compound of Formula 2 (see Reaction Scheme 1) is reacted with by tributyl(1-ethoxyvinyl)tin in the presence dichlorobis (triphenylphosphine)palladium(II) under an inert gas (argon) atmosphere in an aprotic neutral solvent, such as tetrahydrofuran (THF), to provide a 6-acetylchroman derivative of Formula 25. The 6-acetylchroman derivative of Formula 25 is then reacted with iodine and silver(I)trifluoromethanesulfonate (AgOTf) to give a 6-acetyl-8-iodochroman derivative of Formula 26. The compound of Formula 26 is reacted with with trimethylsilyl acetylene in triethyl amine under argon atmosphere in the presence of copper(I)iodide and dichlorobis(triphenylphosphine)palladium(II) (Pd (PPh$_3$)$_2$Cl$_2$) to give the 6-acetyl-8-trimethylsilanyl-ethynyl-chroman derivative of Formula 27. The latter reaction is analogous to the conversion of the 8-iodo-substituted chroman compounds of Formula 4 to the 8-trimethylsilanyl-ethynyl-chroman derivatives of Formula 5, as shown in Reaction Scheme 1.

The acetyl group of 6-acetyl-8-trimethylsilanyl-ethynyl-, chroman derivative of Formula 27 is then converted into an ethynyl group by treatment with lithium di-iso-propyl amide and diethyl chlorophosphate and subsequently with lithium di-iso-propyl amide, to give the 6-ethynyl-8-trimethylsilanyl-ethynyl-chroman derivative of Formula 28. For this reaction lithium di-iso-propyl amide is generated from N,N-di-iso-propyl amine with n-butyl lithium in an aproptic solvent, such as THF and/or hexanes. A more detailed description of this reaction of converting a 6-acetyl-chroman derivative into a 6-ethynyl-chroman is given in U.S. Pat. No. 4,980,369 which is incorporated herein by reference. The 6-ethynyl-8-trimethylsilanyl-ethynyl-chroman derivative of Formula 28 is reacted in the presence of cuprous iodide (CuI) with an iodo-benzoic acid ester or iodo-phenylacetic ester derivative of Formula 29, where the variables R$_3$, o and p are defined as in connection with Formula 1, and R' is an alkyl group of 1 to 6 carbons, preferably methyl or ethyl. Examples for the iodo-benzoic acid ester or iodo-phenylacetic ester derivative of Formula 29 are ethyl 4-iodobenzoate and methyl 4-iodoacetate. The preparation of ethyl 4-iodo benzoate is described in U.S. Pat. No. 4,980,369, and the preparation of 4-iodo phenyl acetic acid methyl ester is described in U.S. Pat. No. 6,252,090, incorporated herein by reference. Generally speaking, the reagents of Formula 29 can be obtained in accordance with the chemical patent and scientific literature, or by such modifications of said literature that is readily apparent to those skilled in the art.

The reaction between the 6-ethynyl-8-trimethylsilanyl-ethynyl-chroman derivative of Formula 28 and the reagent of Formula 29 is conducted under an argon atmosphere, in the presence of copper(I)iodide and dichlorobis(triphenylphosphine)palladium(II) in triethylamine. A more detailed general description of this reaction can be found in U.S. Pat. No. 4,980,369. The product of the latter reaction is a (8-trimethylsilanyl-ethynyl-chroman-6-yl-ethynyl)-benzoic acid ester or (8-trimethylsilanyl-ethynyl-chroman-6-yl-ethynyl)-phenylacetic acid ester of Formula 30. The trimethylsilyl blocking group is removed and the ester group is saponified from the compound of Formula 30 by treatment with aqueous base, to give the (8-ethynyl-chroman-6-yl-ethynyl)-benzoic acid or (8-ethynyl-chroman-6-yl-ethynyl)-phenylacetic acid derivatives of Formula 31. The compounds of Formula 31 are within the scope of the invention and within the scope of Formula 1.

Compounds of the invention where the variable Y is an ethynyl-methyl group and the variable Z is an ethynyl group can, generally speaking, be obtained in accordance with Reaction Scheme 16.

REACTION SCHEME 16

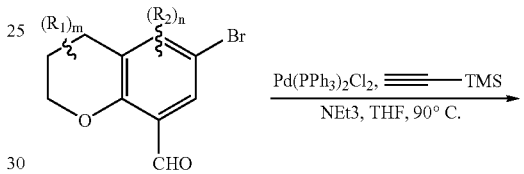

U.S. Patent No. 6,303,785
Formula 32

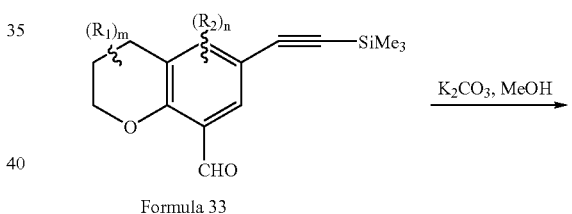

Formula 33

Formula 34

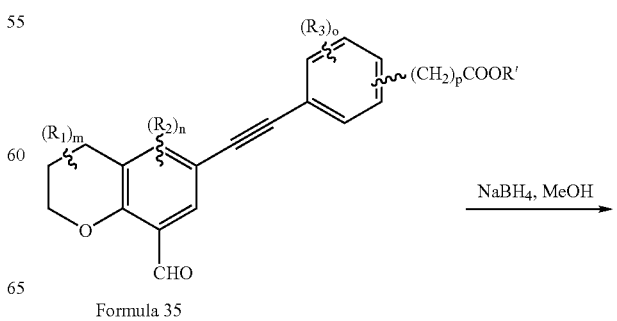

Formula 35

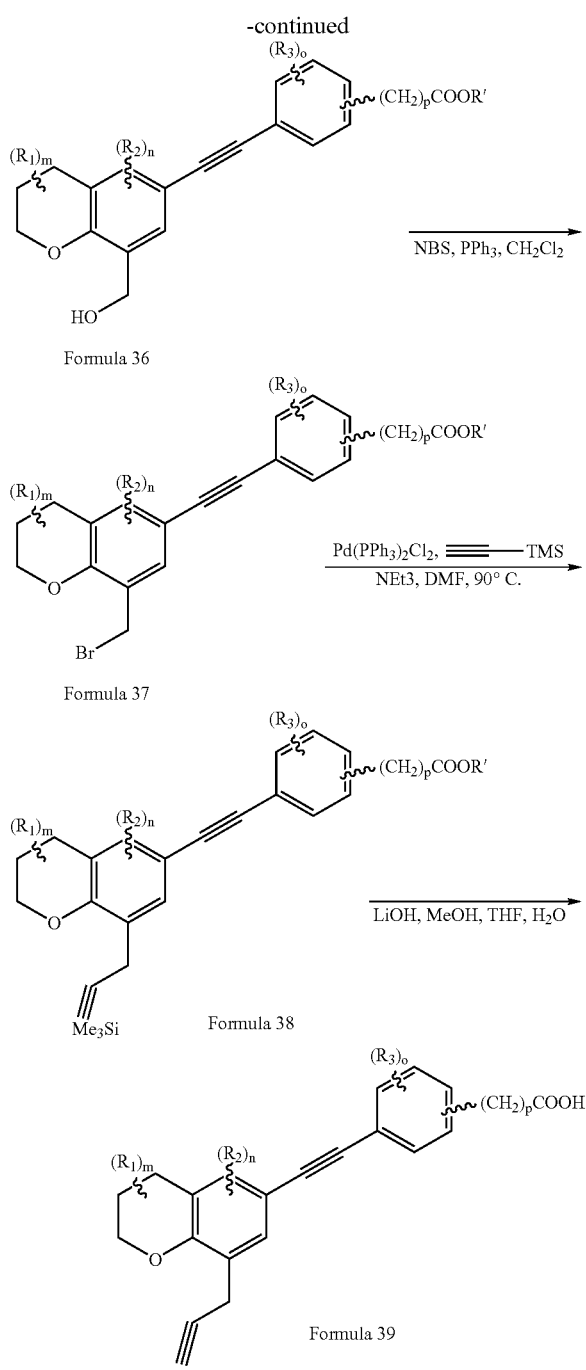

Formula 36

Formula 37

Formula 38

Formula 39

A 6-bromo-chroman-8-carbaldehyde derivative of Formula 32 serves as the starting material in this scheme. An example of a compound of Formula 32 that serves as the starting material for several preferred compounds of the present invention is 6-bromo-2,2,4,4-tetramethyl chroman-8-carbaldehyde the synthesis of which is described in U.S. Pat. No. 6,303,785, incorporated herein by reference. Generally speaking compounds of Formula 32 can be obtained as described in U.S. Pat. No. 6,303,785, or by such modifications of this and other known synthetic procedures which are within the skill of the ordinary practitioner in the art. The 6-bromo-chroman-8-carbaldehyde derivative of Formula 32 is reacted under an argon atmosphere with trimethylsilyl acetylene, in the presence of copper(I)iodide and dichlorobis (triphenylphosphine)palladium(II) in triethylamine and tetrahydrofuran as the solvent. The trimethylsilyl blocking group is removed from the resulting 6-trimethylsilanyl-ethynyl-tetramethyl chroman-8-carbaldehyde of Formula 33 by treatment with base, such as potassium carbonate, to give a 6-ethynyl-tetramethyl chroman-8-carbaldehyde derivative of Formula 34. The 6-ethynyl-tetramethyl chroman-8-carbaldehyde derivative of Formula 34 is reacted with an iodo-benzoic acid ester or iodo-phenylacetic ester derivative of Formula 29 (see Reaction Scheme 15) to provide an (8-formyl-chroman-6-yl-ethynyl)-benzoic acid ester or (8-formyl-chroman-6-yl-ethynyl)-phenylacetic acid ester of Formula 35.

The aldehyde function of the (8-formyl-chroman-6-yl-ethynyl)-benzoic acid ester or (8-formyl-chroman-6-yl-ethynyl)-phenylacetic acid ester of Formula 35 is reduced by treatment with sodium borohydride, and the resulting primary alcohol of Formula 36 is treated under an inert gas (argon) atmosphere with N-bromo succinimide in the presence of triphenylphosphine in an anhydrous solvent, such as dichloromethane, to give an (8-bromomethyl-chroman-6-yl-ethynyl)-benzoic acid ester or (8-bromomethyl-chroman-6-yl-ethynyl)-phenylacetic acid ester of Formula 37. The bromo compound of Formula 37 is reacted with trimethylsilyl acetylene, in the presence of copper(I)iodide and dichlorobis(triphenylphosphine)palladium(II) in triethylamine and dimethylformamide as the solvent to provide (8-3-trimethylsilanyl-prop-2-ynyl -chroman-6-yl-ethynyl)-benzoic acid ester or (8-3-trimethylsilanyl-prop-2-ynyl -chroman-6-yl-ethynyl)-phenylacetic acid ester derivatives of Formula 38. Treatment of the compounds of Formula 38 with aqueous base removes the trimethylsilyl protective group and saponifies the ester function to yield (8-prop-2-ynyl-chroman-6-yl-ethynyl)-benzoic acid or (8-prop-2-ynyl-chroman-6-yl-ethynyl)-phenylacetic acid derivatives of Formula 39. The compounds of Formula 39 are within the scope of the invention and within the scope of Formula 1.

Reaction Scheme 17 discloses the presently preferred synthetic process for obtaining the preferred exemplary compounds of the invention where the variable Z is an ester (COO) and the variable Y is cyano (CN).

Reaction Schemes 18 and 19 disclose the presently preferred synthetic processes for obtaining the preferred exemplary compounds of the invention where the variable Z is ethynyl and the variable Y is ethynyl or ethynylmethyl, respectively. A detailed description of the reagents and reactions utilized in these synthetic routes is provided in the experimental section.

REACTION SCHEME 17

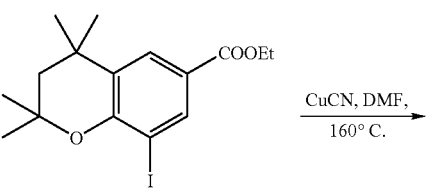

Compound 24

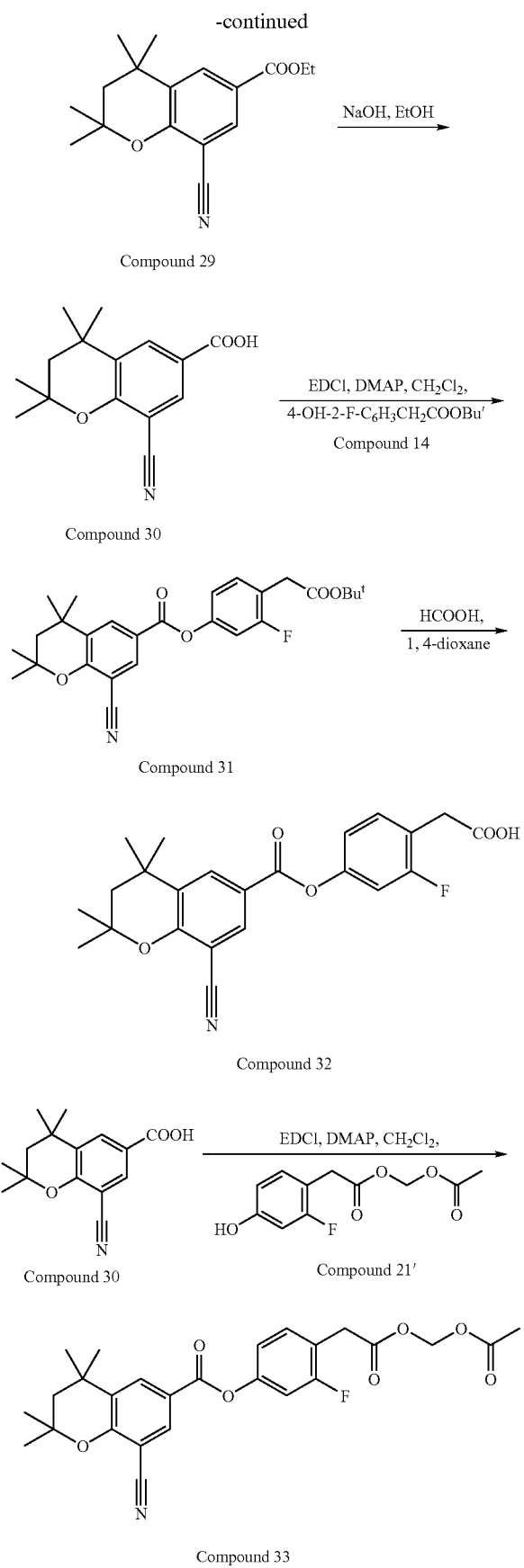
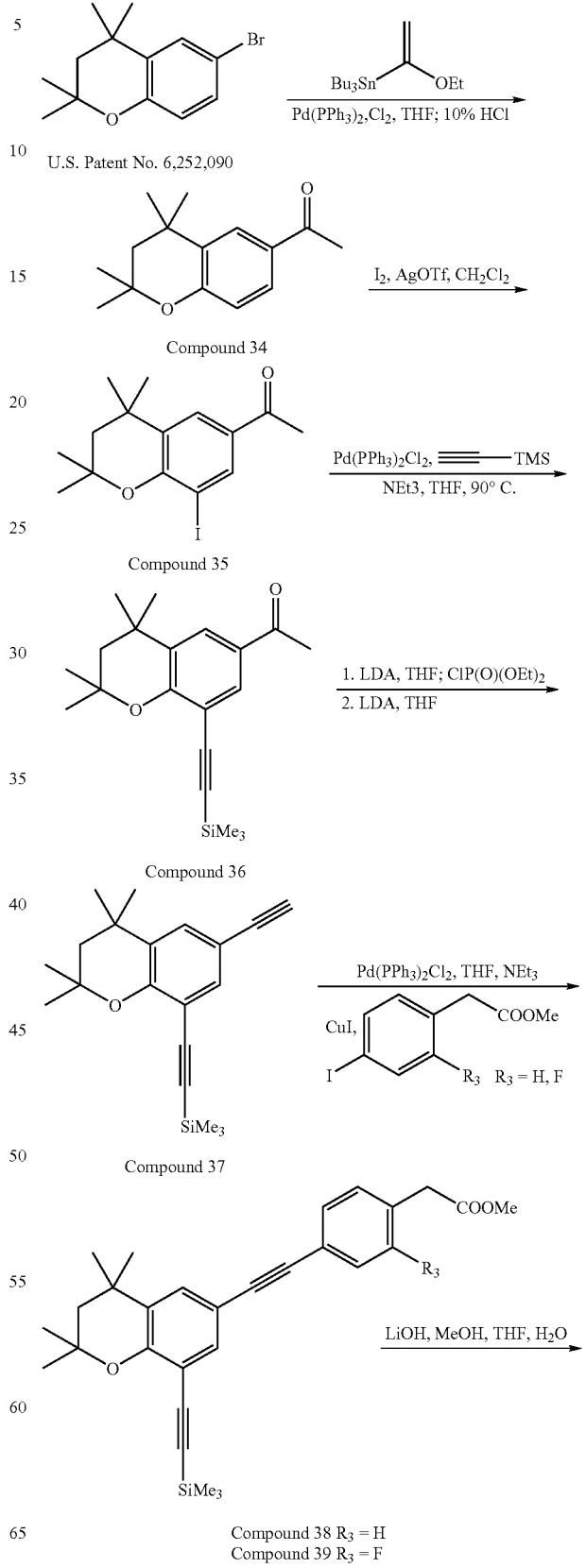
REACTION SCHEME 18

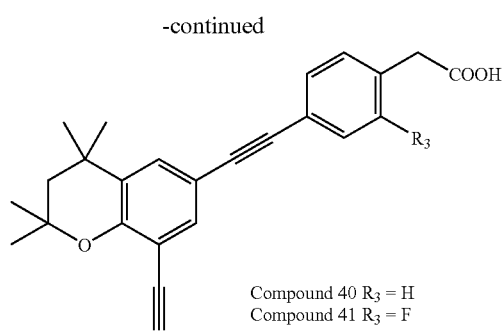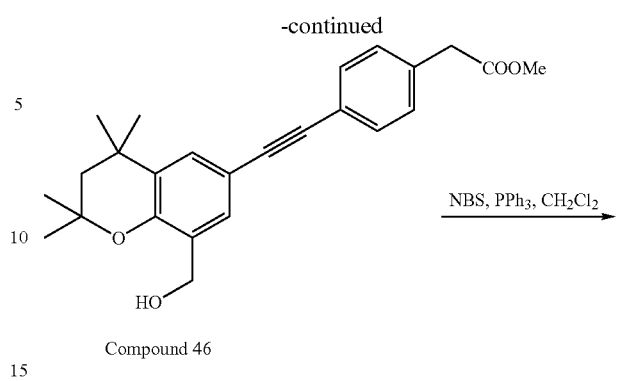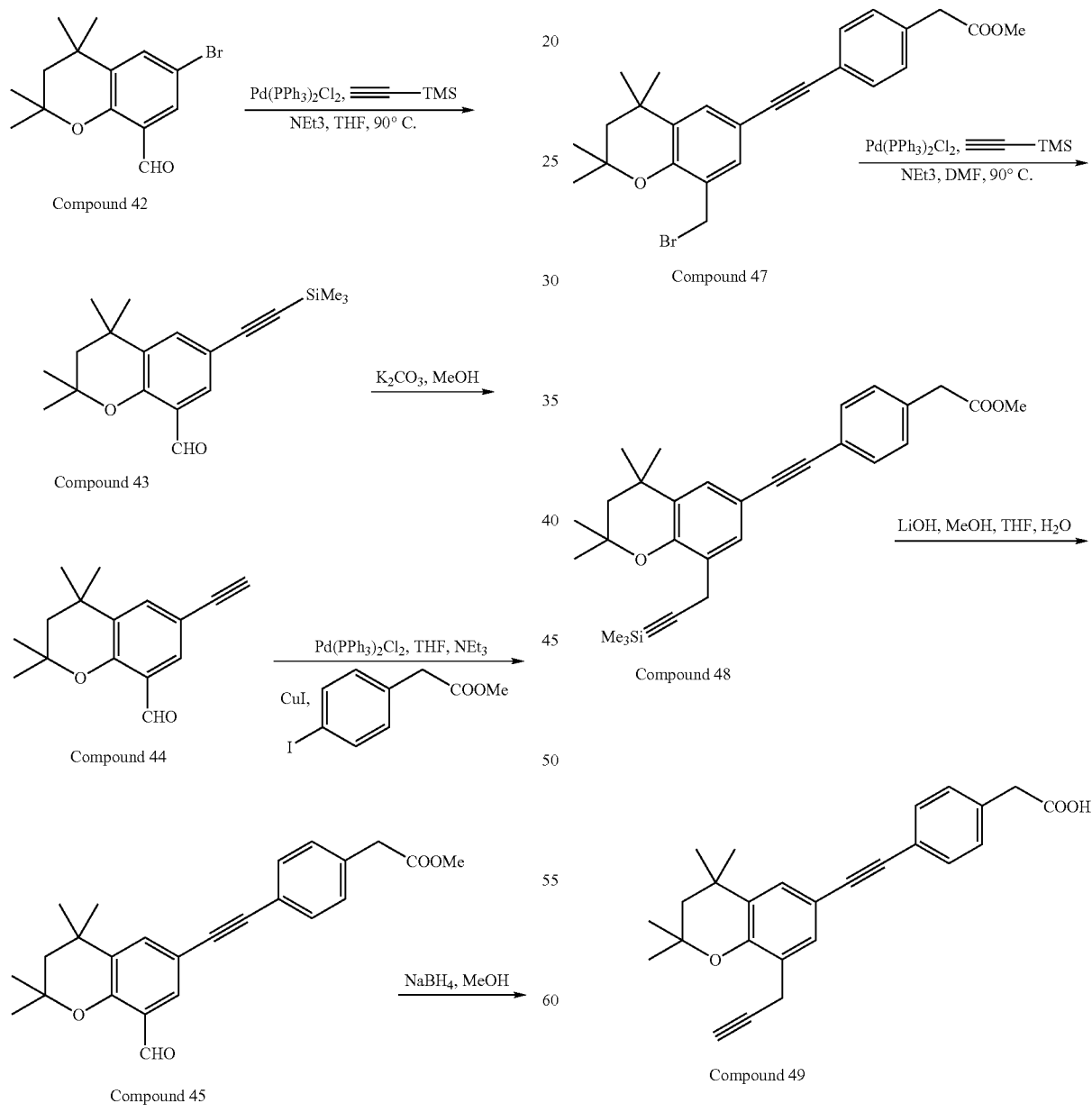

SPECIFIC EXAMPLES

Ethyl-2,2,4,4-tetramethyl chroman-6-carboxylate (Compound 23)

A solution of 6-bromo-2,2,4,4-tetramethylchroman (synthesis is described in U.S. Pat. No. 6,252,090)(2.2 g, 8.08 mmol), palladium acetate (0.145 g, 0.65 mmol) and 1,3-bis(diphenylphosphino)propane (0.267 g, 0.65 mmol) in a mixture of N,N-dimethylformamide (25 mL), ethanol (20 mL) and triethyl amine (7 mL) was heated at 90° C. under an atmosphere of carbon monoxide overnight. The volatiles were distilled off in vacuo and the residue was diluted with water and extracted with ethyl acetate. The combined organic extract was washed with brine (×1), dried over anhydrous magnesium sulfate, filtered and evaporated in vacuo to an oil which was subjected to flash column chromatography over silica gel (230-400 mesh) using 5-10% ethyl acetate in hexane as the eluent to afford the title compound (1.9 g, 90%).

$^1$H NMR (300 MHz, CDCl$_3$): δ8.00 (d, 1H, J=2.3 Hz), 7.76 (dd, 1H, J=2.1, 8.5 Hz), 6.79 (d, 1H, J=8.5 Hz), 4.33 (q, 2H, J=7.1 Hz), 1.85 (s, 2H), 1.36 (s, 6H), 1.37 (s, 6H), 1.39–1.33 (m, 3H).

General Procedure B: Ethyl-8-iodo-2,2,4,4-tetramethyl chroman-6-carboxylate (Compound 24)

A solution of ethyl-2,2,4,4-tetramethyl chroman-6-carboxylate (Compound 23, 0.733 g, 2.8 mmol) in anhydrous dichloromethane (10 mL) was treated with silver(I)trifluoromethanesulfonate (0.719 g, 2.8 mmol) and iodine (0.71 g, 2.8 mmol) and the resulting solution was stirred at ambient temperature for 4 h. The reaction mixture was treated with saturated, aqueous sodium thiosulfate solution and extracted with ethyl acetate. The organic phase was dried over anhydrous magnesium sulfate, filtered and evaporated in vacuo to a residue which was subjected to flash column chromatography over silica gel (230-400mesh) using 5-10% ethyl acetate in hexane as the eluent to afford the title compound (0.88 g, 81%) as a pale yellow oil.

$^1$H NMR (300 MHz, CDCl$_3$): δ8.26 (d, 1H, J=2.0 Hz), 7.96 (d, 1H, J=2.0 Hz), 4.34 (q, 2H, J=7.1 Hz), 1.87 (s, 2H), 1.40 (s, 6H), 1.37 (s, 6H), 1.41–1.35 (m, 3H).

General procedure C: Ethyl-8-trimethylsilanyl-ethynyl-2,2,4,4-tetramethyl chroman-6-carboxylate (Compound 25)

A solution of ethyl-8-iodo-2,2,4,4-tetramethyl chroman-6-carboxylate (Compound 24, 0.88 g, 2.26 mmol) in triethyl amine (10 mL) was treated with copper(I)iodide (0.043 g, 0.226 mmol) and sparged with argon for 5 minutes. Trimethylsilyl acetylene (3 mL, 21.22 mmol) was then added followed by dichlorobis(triphenylphosphine)palladium(II) (0.159 g, 0.226 mmol). The resulting reaction mixture was heated at 70° C. overnight in a sealed tube. It was then cooled to ambient temperature, diluted with diethyl ether and filtered over a bed of celite. The filtrate was evaporated in vacuo to an oil which was subjected to flash column chromatography over silica gel (230-400 mesh) using 10% ethyl acetate in hexane as the eluent to afford the title compound (0.803 g, 99%).

$^1$H NMR (300 MHz, CDCl$_3$): δ7.93 (s, 1H), 7.92 (s, 1H), 4.32 (q, 2H, J=7.0 Hz), 1.86 (s, 2H), 1.38 (s, 6H), 1.34 (s, 6H), 1.38–1.34 (m, 3H), 0.24 (s, 9H).

8-Ethynyl-2,2,4,4-tetramethyl chroman-6-carboxylic acid (Compound 26)

A solution of ethyl-8-trimethylsilanyl-ethynyl-2,2,4,4-tetramethylchroman-6-carboxylate (Compound 25, 0.525 g, 1.47 mmol) in ethanol (5 mL) was treated with 2N aqueous sodium hydroxide solution (5 mL, 10 mmol) and the resulting solution was adjusted to pH~5 with 10% aqueous hydrochloric acid and extracted with ethyl acetate. The organic phase was dried over anhydrous magnesium sulfate, filtered and evaporated in vacuo to afford the title product as a brown solid (0.316 g, 84%).

$^1$H NMR (300 MHz, CDCl$_3$): δ8.02 (s, 2H), 3.23 (s, 1H), 1.89 (s, 2H), 1.42 (s, 6H), 1.38 (s, 6H).

General Procedure D: 8-Ethynyl-2,2,4,4-tetramethyl chroman-6-carboxylic acid 4-tert-butoxycarbonylmethyl-phenyl ester (Compound 27)

A solution of 8-ethynyl-2,2,4,4-tetramethyl chroman-6-carboxylic acid (Compound 26, 0.177 g, 0.6 mmol) in anhydrous dichloromethane (10 mL) was treated with tert-butyl-4-hydroxy phenyl acetate (synthesis described in U.S. Pat. No. 6,252,090) (Compound 6, 0.21 g, 1.03 mmol) followed by 1-(3-dimethylaminopropyl)-3-ethylcarbodiimide hydrochloride (0.19 g, 1.03 mmol) and 4-(dimethylamino)pyridine (0.168 g, 1.37 mmol). The resulting solution was stirred at ambient temperature overnight. The reaction mixture was diluted with dichloromethane, washed with water and brine (×1), dried over anhydrous magnesium sulfate, filtered and evaporated in vacuo to a residue that was subjected to flash column chromatography over silica gel (230-400 mesh) using 20% ethyl acetate in hexane as the eluent to afford the title compound as a white solid (0.23 g, 76%).

$^1$H NMR (300 MHz, CDCl$_3$): δ8.14 (d, 1H, J=2.3 Hz), 8.11 (d, 1H, J=2.3 Hz), 7.32 (d, 2H, J=8.5 Hz), 7.14 (d, 2H, J=8.5 Hz), 3.54 (s, 2H), 3.25 (s, 1H), 1.91 (s, 2H), 1.45 (s, 9H), 1.44 (s, 6H), 1.40 (s, 6H).

General Procedure E: 8-Ethynyl-2,2,4,4-tetramethyl-chroman-6-carboxylic acid 4-carboxymethyl-phenyl ester (Compound 1)

A solution of 8-ethynyl-2,2,4,4-tetramethyl chroman-6-carboxylic acid 4-tert-butoxycarbonylmethyl-phenyl ester (Compound 27, 1.5 g, 3.34 mmol) in 1,4-dioxane (30 mL) was treated with formic acid (200 mL) at ambient temperature. After 2 h, the reaction mixture was diluted with water and extracted with diethyl ether. The organic phase was dried over anhydrous magnesium sulfate, filtered and evaporated in vacuo to afford the title product. The product was further purified by recrystallization from 10-20% ethyl acetate in hexane (1.32 g, 100%).

$^1$H NMR (300 MHz, CDCl$_3$): δ8.11 (d, 1H, J=2.0 Hz), 8.07 (d, 1H, J=2.0 Hz), 7.34 (d, 2H, J=8.5 Hz), 7.15 (d, 2H, J=8.5 Hz), 3.66 (s, 2H), 3.24 (s, 1H), 1.90 (s, 2H), 1.43 (s, 6H), 1.39 (s, 6H).

Ethyl-4-hydroxy phenyl acetate (Compound 15)

A solution of 4-hydroxy phenyl acetic acid (4.5 g, 29.57 mmol) in benzene (60 mL) and ethanol (60 mL) was treated with concentrated sulfuric acid (2 mL) and heated to reflux overnight using a Dean-Stark water trap. The volatiles were evaporated in vacuo, the residue was diluted with water and extracted with diethyl ether (×2). The combined organic phase was washed with water (×1) and brine (×1), dried over anhydrous magnesium sulfate, filtered over a short bed of silica gel and evaporated in vacuo to afford the title product as an oil (5 g, 94%).

$^1$H-NMR (300 MHz, CDCl$_3$): δ1.23 (t, J=6.7 Hz, 3H), 3.52 (s, 2H), 4.14 (q, J=6.7 Hz, 2H), 6.70 (d, J=8.2 Hz, 2H), 7.06 (d, J=8.5 Hz, 2H).

8-Ethynyl-2,2,4,4-tetramethyl-chroman-6-carboxylic acid 4-ethoxycarbonylmethyl-phenyl ester (Compound 2)

Following General Procedure D and using 8-ethynyl-2,2,4,4-tetramethyl chroman-6-carboxylic acid (Compound 26, 0.45 g, 1.75 mmol), anhydrous dichloromethane (20 mL), ethyl-4-hydroxy phenyl acetate (Compound 15, 0.38 g, 2.1 mmol), 1-(3-dimethylaminopropyl)-3-ethylcarbodiimide hydrochloride (0.5 g, 2.62 mmol) and 4-(dimethylamino) pyridine (0.43 g, 3.5 mmol) followed by flash column chromatography over silica gel (230-400 mesh) using 20% ethyl acetate in hexane as the eluent, the title compound was obtained as white solid (0.536 g, 74%).

$^1$H NMR (300 MHz, CDCl$_3$): δ8.14 (d, 1H, J=2.1 Hz), 8.11 (d, 1H, J=2.1 Hz), 7.34 (d, 2H, J=8.5 Hz), 7.15 (d, 2H, J=8.5 Hz), 4.16 (q, 2H, J=7.0 Hz), 3.62 (s, 2H), 3.26 (s, 1H), 1.90 (s, 2H), 1.43 (s, 6H), 1.40 (s, 6H), 1.26 (t, 3H, J=7.0 Hz).

General Procedure F: Methyl-4-benzyloxyphenyl acetate (Compound 16)

A solution of methyl-4-hydroxy phenyl acetate (8.5 g, 50 mmol) in acetone (100 mL) was treated with potassium carbonate (13.83 g, 100 mmol) followed by benzyl bromide (6.54 mL, 55 mmol) and the resulting solution was refluxed overnight. The reaction mixture was then cooled to ambient temperature and the solids were removed by filtration and were washed with acetone. The combined filtrate and washings were evaporated in vacuo to afford the title product (12.08 g, 94%) that was used as such for the next step without purification.

$^1$H-NMR (300 MHz, CDCl$_3$): δ3.63 (s, 2H), 3.74 (s, 3H), 5.1 (s, 2H), 7.01 (d, J=8.8 Hz, 2H), 7.27 (d, J=8.8 Hz, 2H), 7.38-7.51 (m, 5H).

4-Benzyloxy phenyl acetic acid (Compound 17)

A solution of methyl-4-benzyloxyphenyl acetate (Compound 16, 12.08 g, 47.2 mmol) in a mixture of methanol (45 mL), tetrahydrofuran (40 mL) and water (15 mL) was treated with lithium hydroxide monohydrate (5 g, 119 mmol) and the resulting reaction mixture was stirred at ambient temperature for 1 h. The precipitated solid in the reaction mixture was filtered and washed well with diethyl ether. The white solid was then dissolved in dilute, aqueous hydrochloric acid and the solution was extracted with ethyl acetate (×2). The combined organic extracts were dried over anhydrous magnesium sulfate, filtered and evaporated in vacuo to afford the title product as a white solid (11 g, 96%).

$^1$H-NMR (300 MHz, CDCl$_3$): δ3.55 (s, 2H), 5.01 (s, 2H), 6.92 (d, J=8.5 Hz, 2H), 7.17 (d, J=8.5 Hz, 2H), 7.30-7.42 (m, 5H), 11.00-11.50 (br s, 1H).

Acetoxymethyl-4-benzyloxy phenyl acetate (Compound 18)

A solution of 4-benzyloxy phenyl acetic acid (Compound 17, 2 g, 8.26 mmol) in anhydrous acetonitrile (20 mL) was treated with N,N-diisopropyl ethyl amine (3.5 mL, 20 mmol) followed by acetoxy methyl bromide/bromo methylacetate (2.5 g, 16.33 mmol) and the resulting reaction mixture was stirred overnight at ambient temperature. The volatiles were evaporated in vacuo and the residue was diluted with water and extracted with diethyl ether (×2). The combined organic extracts were dried over anhydrous magnesium sulfate, filtered and evaporated in vacuo to an oil that was subjected to flash column chromatography over silica gel (230-400 mesh) using 16% ethyl acetate in hexane as the eluent to afford the title compound as an oil (95% pure, 1.43 g, 55%).

$^1$H-NMR (300 MHz, CDCl$_3$): δ2.04 (s, 3H), 3.60 (s, 2H), 5.02 (s, 2H), 5.74 (s, 2H), 6.95 (d, J=8.5 Hz, 2H), 7.19 (d, J=8.5 Hz, 2H), 7.31-7.44 (m, 5H).

General Procedure G: Acetoxymethyl-4-hydroxy phenyl acetate (Compound 19)

A solution of acetoxymethyl-4-benzyloxy phenyl acetate (Compound 18, 1.42 g, 4.52 mmol) in ethyl acetate (20 mL) was treated with a slurry of 5% palladium on carbon (0.5 g) and the resulting reaction mixture was stirred overnight at ambient temperature under an atmosphere of hydrogen. The reaction mixture was then diluted with dichloromethane and filtered over a bed of celite. The filtrate and washings were evaporated in vacuo to afford the title compound as an oil (1 g, 92.5%).

$^1$H-NMR (300 MHz, CDCl$_3$): δ2.05 (s, 3H), 3.57 (s, 2H), 5.72 (s, 2H), 6.74 (d, J=8.5 Hz, 2H), 7.07 (d, J=8.2 Hz, 2H).

8-Ethynyl-2,2,4,4-tetramethyl-chroman-6-carboxylic acid 4-acetoxymethoxycarbonylmethyl-phenyl ester (Compound 3)

Following General Procedure D and using 8-ethynyl-2,2,4,4-tetramethyl chroman-6-carboxylic acid (Compound 26, 0.416 g, 1.66 mmol), anhydrous dichloromethane (20 mL), acetoxymethyl-4-hydroxy phenyl acetate (Compound 19 0.433 g, 1.99 mmol), 1-(3-dimethylaminopropyl)-3-ethylcarbodiimide hydrochloride (0.464 g, 2.42 mmol) and 4-(dimethylamino)pyridine (0.39 g, 3.22 mmol) followed by flash column chromatography over silica gel (230-400 mesh) using 25% ethyl acetate in hexane as the eluent, the title compound was obtained as a white solid (0.55 g, 73%).

$^1$H NMR (300 MHz, CDCl$_3$): δ8.11 (d, 1H, J=2.0 Hz), 8.09 (d, 1H, J=2.0 Hz), 7.33 (d, 2H, J=8.5 Hz), 7.16 (d, 2H, J=8.5 Hz), 5.75 (s, 2H), 3.66 (s, 2H), 3.24 (s, 1H), 2.09 (s, 3H), 1.90 (s, 2H), 1.43 (s, 6H), 1.39 (s, 6H).

4-Benzyloxy-2-fluoro-benzonitrile (Compound 7)

Following General Procedure F and using 2-fluoro-4-hydroxy-benzonitrile (11.37 g, 83 mmol), acetone (100 mL), potassium carbonate (30 g, 165.8 mmol) followed by benzyl bromide (10.84 mL, 91 mmol) the title product (18 g, 96%) was obtained.

$^1$H-NMR (300 MHz, CDCl$_3$): δ5.10 (s, 2H), 6.75-6.85 (m, 2H), 7.25-7.54 (m, 6H).

4-Benzyloxy-2-fluoro-benzaldehyde (Compound 8)

A stirred, cooled (−78° C.) solution of 4-benzyloxy-2-fluoro-benzonitrile (Compound 7, 18 g, 79 mmol) in dichloromethane (50 mL) was treated with a 1M solution of di-isobutyl aluminum hydride in hexanes (100 mL, 100 mmol). The reaction mixture was allowed to warm to ambient temperature over 1 h. It was then quenched with aqueous dilute hydrochloric acid and extracted with diethyl ether (×2). The combined organic phase was dried over anhydrous magnesium sulfate, filtered and evaporated in vacuo to afford the title product as a white solid (16 g, 88%).

$^1$H-NMR (300 MHz, CDCl$_3$): δ5.11 (s, 2H), 6.70 (dd, J=12.3, 2.3 Hz, 1H), 6.82-6.86 (m, 1H), 7.24-7.42 (m, 5H), 7.81 (t, J=8.9 Hz, 1H), 10.19 (s, 1H).

4-Benzyloxy-2-fluoro-benzyl alcohol (Compound 9)

A solution of 4-benzyloxy-2-fluoro benzaldehyde (Compound 8, 16 g, 69.6 mmol) in methanol (100 mL) and dichloromethane (100 mL) was treated with sodium borohydride (5.26 g, 139 mmol). After 2 h at ambient temperature, the volatiles were evaporated in vacuo, the residue was diluted with water and dilute aqueous hydrochloric acid and extracted with diethyl ether (×2). The combined organic phase was dried over anhydrous magnesium sulfate, filtered and evaporated in vacuo to afford the title product as a white solid (15 g, 95%).

$^1$H-NMR (300 MHz, CDCl$_3$): δ2.13 (s, 1H), 4.61 (s, 2H), 5.01 (s, 2H), 6.64-6.74 (m, 2H), 7.25 (t, J=8.2 Hz, 1H), 7.29-7.42 (m, 5H).

4-Benzyloxy-2-fluoro-benzyl bromide (Compound 10)

A stirred, cooled (ice bath) solution of 4-benzyloxy-2-fluoro-benzyl alcohol (Compound 9, 15 g, 64.6 mmol) in anhydrous diethyl ether (100 mL) was treated with pyridine (5.75 mL, 71.1 mmol) followed by phosphorus tribromide (6.13 mL, 64.6 mmol). After 90 min. the reaction mixture was diluted with water and extracted with diethyl ether (×2). The combined organic phase was dried over anhydrous magnesium sulfate, filtered and evaporated in vacuo to afford the title product as an oil that solidified on standing (18 g, 89.5%).

$^1$H-NMR (300 MHz, CDCl$_3$): δ4.48 (s, 2H), 5.02 (s, 2H), 6.65-6.74 (m, 2H), 7.26 (t, J=8.5 Hz, 1H), 7.31-7.39 (m, 5H).

4-Benzyloxy-2-fluoro-phenyl acetic acid (Compound 12)

A solution of 4-benzyloxy-2-fluoro-benzyl bromide (Compound 10, 18 g, 58 mmol) in a mixture of ethanol (90 mL) and water (10 mL) was treated with sodium cyanide (4.25 g, 86,8 mmol) and the resulting reaction mixture was heated at 70° C. for 1 h. Potassium hydroxide (6.5 g, 115.7 mmol) was then added and heating was continued for another 5 h. The volatiles were evaporated in vacuo, the residue was diluted with water and neutralized with hydrochloric acid and the precipitated solid was filtered, washed with water and dried to afford the title product as a yellow solid (13 g, 81%).

$^1$H-NMR (300 MHz, CDCl$_3$): δ3.60 (s, 2H), 5.01 (s, 2H), 6.67-6.74 (m, 2H), 7.12 (t, J=8.2 Hz, 1H), 7.23-7.41 (m, 5H), 9.74 (br s, 1H).

Tert-butyl-4-benzyloxy-2-fluoro-phenyl acetate (Compound 13)

A solution of 4-benzyloxy-2-fluoro-phenyl acetic acid (6.5 g, 25 mmol) in anhydrous toluene was heated to 80° C. under argon, then treated with N,N-dimethyl formamide-di-t-butyl acetal (22 mL, 91.75 mmol). After 1 h, the reaction mixture was cooled to ambient temperature, diluted with water and extracted with diethyl ether (×2). The combined organic phase was dried over anhydrous magnesium sulfate, filtered and evaporated in vacuo to afford a residue which after flash column chromatography over silica gel (230-400 mesh) using 10% ethyl acetate in hexane as the eluent afforded the title compound (2.2 g, 28%) and some recovered starting material (1.6 g, 25%).

$^1$H-NMR (300 MHz, CDCl$_3$): δ1.53 (s, 9H), 3.58 (s, 2H), 5.06 (s, 2H), 6.74-6.81 (m, 2H), 7.20 (t, J=8.2 Hz, 1H), 7.38-7.48 (m, 5H).

Tert-butyl-2-fluoro-4-hydroxy-phenyl acetate (Compound 14)

Following General Procedure G and using tert-butyl-4-benzyloxy-2-fluoro-phenyl acetate (Compound 13, 2.2 g, 6.96 mmol), ethyl acetate (15 mL) and 5% palladium on carbon (0.436 g) the title compound was obtained as a white solid (1.5 g, 95%).

$^1$H-NMR (300 MHz, CDCl$_3$): δ1.47 (s, 9H), 3.50 (s, 2H), 6.38-6.48 (m, 2H), 6.95 (t, J=8.2 Hz, 1H), 7.20 (br s, 1H).

8-Ethynyl-2,2,4,4-tetramethyl chroman-6-carboxylic acid-3-fluoro-4-tert-butoxycarbonylmethyl-phenyl ester (Compound 28)

Following General Procedure D and using 8-ethynyl-2,2,4,4-tetramethyl chroman-6-carboxylic acid (Compound 26, 0.107 g, 0.415 mmol), anhydrous dichloromethane (10 mL), tert-butyl-2-fluoro-4-hydroxy phenyl acetate (Compound 14, 0.14 g, 0.62 mmol), 1-(3-dimethylaminopropyl)-3-ethylcarbodiimide hydrochloride (0.12 g, 0.62 mmol) and 4-(dimethylamino)pyridine (0.101 g, 0.83 mmol) followed by flash column chromatography over silica gel (230-400 mesh) using 10-15% ethyl acetate in hexane as the eluent, the title compound was obtained as a pale yellow solid (0.156 g, 92%).

$^1$H NMR (300 MHz, CDCl$_3$): δ8.12 (d, 1H, J=2.1 Hz), 8.10 (d, 1H, J=2.1 Hz), 7.31 (t, 1H, J=8.2 Hz), 7.01–6.97 (m, 2H), 3.60 (s, 2H), 3.27 (s, 1H), 1.91 (s, 2H), 1.46 (s, 9H), 1.44 (s, 6H), 1.40 (s, 6H).

8-Ethynyl-2,2,4,4-tetramethyl-chroman-6-carboxylic acid-4-carboxymethyl-3-fluoro-phenyl ester (Compound 4)

Following General Procedure E and using 8-ethynyl-2,2,4,4-tetramethyl chroman-6-carboxylic acid-3-fluoro-4-tert-butoxycarbonylmethyl-phenyl ester (Compound 28, 0.085 g, 0.21 mmol), 1,4-dioxane (2 mL) and formic acid (8 mL) followed by recrystallization from 10-20% ethyl acetate in hexane, the title compound was obtained (0.055 g, 75%).

$^1$H NMR (300 MHz, CDCl$_3$): δ8.13 (d, 1H, J=2.0 Hz), 8.10 (d, 1H, J=2.0 Hz), 7.34 (t, 1H, J=8.2 Hz), 7.04–7.00 (m, 2H), 3.75 (s, 2H), 3.28 (s, 1H), 1.93 (s, 2H), 1.46 (s, 6H), 1.42 (s, 6H).

Acetoxymethyl-2-fluoro-4-benzyloxy phenyl acetate (Compound 20)

A solution of 4-benzyloxy-2-fluoro-phenyl acetic acid (Compound 12, 2.06 g, 7.92 mmol) in anhydrous acetonitrile (20 mL) was treated with N,N-diisopropyl ethyl amine (3.45 mL, 19.8 mmol) followed by acetoxy methyl bromide/bromo methylacetate (2.37 g, 15.84 mmol) and the resulting reaction mixture was stirred at ambient temperature for 6 h. The reaction mixture was diluted with water and extracted with diethyl ether. The combined organic phase was dried over anhydrous magnesium sulfate, filtered and evaporated in vacuo to an oil that was subjected to flash column chromatography over silica gel (230-400 mesh) using 10-20% ethyl acetate in hexane as the eluent to afford the title compound as a white solid (1.5 g, 57%).

$^1$H-NMR (300 MHz, CDCl$_3$): δ2.11 (s, 3H), 3.65 (s, 2H), 5.04 (s, 2H), 5.76 (s, 2H), 6.69-6.75 (m, 2H), 7.15 (t, J=9.0 Hz, 1H), 7.35-7.41 (m, 5H).

Acetoxymethyl-2-fluoro-4-hydroxy-phenyl acetate (Compound 21)

Following General Procedure G and using acetoxymethyl-4-benzyloxy-2-fluoro-phenyl acetate (Compound 20, 0.75 g, 2.26 mmol), ethyl acetate (15 mL) and 10% palladium on carbon (0.08 g), the title compound was obtained as an oil (0.48 g, 88%). $^1$H-NMR (300 MHz, CDCl$_3$): δ2.09 (s, 3H), 3.62 (s, 2H), 5.75 (s, 2H), 6.48-6.54 (m, 2H), 7.02 (d, J=8.4 Hz, 1H).

8-Ethynyl-2,2,4,4-tetramethyl-chroman-6-carboxylic acid 4-acetoxymethoxycarbonylmethyl-3-fluoro-phenyl ester (Compound 5)

Following General Procedure D and using 8-ethynyl-2,2,4,4-tetramethyl chroman-6-carboxylic acid (Compound 26, 0.426 g, 1.65 mmol), anhydrous dichloromethane (20 mL), acetoxymethyl-2-fluoro-4-hydroxy phenyl acetate (Compound 21, 0.48 g, 1.98 mmol), 1-(3-dimethylaminopropyl)-3-ethylcarbodiimide hydrochloride (0.475 g, 2.48 mmol) and 4-(dimethylamino)pyridine (0.403 g, 3.3 mmol) followed by flash column chromatography over silica gel (230-400 mesh) using 25% ethyl acetate in hexane as the eluent, the title compound was obtained as a white solid (0.397 g, 50%).

$^1$H NMR (300 MHz, CDCl$_3$): δ8.12 (d, 1H, J=2.1 Hz), 8.09 (d, 1H, J=2.1 Hz), 7.32 (t, 2H, J=8.1 Hz), 7.03–6.99 (m, 2H), 5.79 (s, 2H), 3.74 (s, 2H), 3.26 (s, 1H), 2.12 (s, 3H), 1.92 (s, 2H), 1.45 (s, 6H), 1.41 (s, 6H).

6-Acetyl-2,2,4,4-tetramethyl chroman (Compound 34)

A solution of 6-bromo-2,2,4,4-tetramethyl chroman (see U.S. Pat. No. 6,252,090, 0.9 g, 3.34 mmol) in anhydrous tetrahydrofuran (50 mL) was sparged with argon for 5 min. and treated with dichlorobis(triphenylphosphine)palladium (II) (0.117 g, 0.167 mmol) followed by tributyl(1-ethoxyvinyl)tin (2.41 g, 6.7 mmol). The resulting reaction mixture was heated at 80° C. under argon for 18 h. The reaction mixture was then cooled to ambient temperature and treated with 10% aqueous hydrochloric acid (5 mL) and stirred for 30 min. The reaction mixture was then diluted with ethyl acetate and washed with water (×1) and brine (×1). The organic phase was dried over anhydrous sodium sulfate, filtered and evaporated in vacuo to afford a residue that was subjected to flash column chromatography over silica gel (230-400 mesh) using 2-3%% ethyl acetate in hexane as the eluent to afford the title compound as a colorless oil (0.36 g, 46%).

$^1$H-NMR (300 MHz, CDCl$_3$): δ7.96 (d, 1H, J=2.1 Hz), 7.70 (dd, 1H, J=2.1, 8.5 Hz), 6.81 (d, 1H, J=8.5 Hz), 2.54 (s, 3H), 1.86 (s, 2H), 1.38 (s, 6H), 1.37 (s, 6H).

General Procedure H:
6-Acetyl-8-iodo-2,2,4,4-tetramethyl chroman (Compound 35)

A solution of 6-acetyl-2,2,4,4-tetramethyl chroman (Compound 34, 0.36 g, 1.55 mmol) in anhydrous dichloromethane (5 mL) was treated with silver(I)trifluoromethanesulfonate (0.398 g, 1.55 mmol) and iodine (0.393 g, 1.55 mmol) and the resulting solution was stirred at ambient temperature for 4 h. The reaction mixture was treated with saturated, aqueous sodium thiosulfate solution and extracted with ethyl acetate. The organic phase was dried over anhydrous magnesium sulfate, filtered and evaporated in vacuo to a residue which was subjected to flash column chromatography over silica gel (230-400 mesh) using 4-10% ethyl acetate in hexane as the eluent to afford the title compound (0.47 g, 85%) as a viscous oil.

$^1$H NMR (300 MHz, CDCl$_3$): δ8.16 (d, 1H, J=2.1 Hz), 7.90 (d, 1H, J=2.1 Hz), 2.52 (s, 3H), 1.86 (s, 2H), 1.38 (s, 6H), 1.37 (s, 6H).

General Procedure I:
6-Acetyl-8-trimethylsilanylethynyl-2 2,4,4-tetramethyl chroman (Compound 36)

A solution of 6-acetyl-8-iodo-2,2,4,4-tetramethyl chroman (Compound 35, 0.8 g, 2.01 mmol) in triethyl amine (8 mL) was treated with copper(I)iodide (0.030 g, 0.16 mmol) and sparged with argon for 5 minutes. Trimethylsilyl acetylene (1 mL, 7.07 mmol) and dichlorobis(triphenylphosphine)palladium(II) (0.113 g, 0.16 mmol) were added sequentially and the resulting reaction mixture was heated at 70° C. overnight in a sealed tube. It was then cooled to ambient temperature, diluted with diethyl ether and filtered over a bed of celite. The filtrate was evaporated in vacuo to an oil which was subjected to flash column chromatography over silica gel (230-400 mesh) using 2-5% ethyl acetate in hexane as the eluent. The title compound (0.616 g, 93%) was obtained as a pale yellow solid.

$^1$H NMR (300 MHz, CDCl$_3$): δ7.92 (d, 1H, J=2.1 Hz), 7.84 (s, 1H, J-2.1 Hz), 2.54 (s, 3H), 1.88 (s, 2H), 1.40 (s, 6H), 1.36 (s, 6H), 0.27 (s, 9H).

6-Ethynyl-8-trimethylsilanylethynyl-2,2,4,4-tetramethyl chroman (Compound 37)

A solution of 6-acetyl-8-trimethylsilanylethynyl-2,2,4,4-tetramethyl chroman (Compound 36, 0.616 g, 1.88 mmol) in anhydrous tetrahydrofuran (3 mL) was cannulated into a stirred, cooled (−78° C.) solution of lithium diisopropyl amide [2.82 mmol in 2 mL of tetrahydrofuran generated from N,N-diisopropyl amine (0.4 mL, 2.82 mmol) and 1.6M solution of n-butyl lithium in hexanes (1.88 mL, 3 mmol)] and the resulting reaction mixture was stirred at the same temperature for 50 min. Diethyl chlorophosphate (0.35 mL, 2.44 mol) was then added and the reaction mixture was allowed to warm to 0° C. over 1.5 h. The reaction mixture was then cannulated into a stirred, cooled (−78° C.) solution of lithium diisopropyl amide [8.46 mmol in 3 mL of tetrahydrofuran generated from N,N-diisopropyl amine (1.2 mL, 8.46 mmol) and 1.6M solution of n-butyl lithium in hexanes (5.64 mL, 9 mmol)]. The reaction mixture was allowed to warm to −30° C. over 2 h. It was then quenched with water and extracted with ethyl acetate. The organic phase was washed with water and brine, dried over anhydrous magnesium sulfate, filtered and evaporated in vacuo to a residue that was subjected to flash column chromatography over silica gel (230-400 mesh) using 1-2.5% ethyl acetate in hexane as the eluent to afford the title compound as a white solid (0.29 g, 50%).

$^1$H NMR(300 MHz, CDCl$_3$): δ7.39 (d, 1H, J=2.1 Hz), 7.36 (s, 1H, J=2.1 Hz), 2.96 (s, 1H), 1.84 (s, 2H), 1.38 (s, 6H), 1.31 (s, 6H), 0.25 (s, 9H).

General Procedure J: F4-(2,2,4,4-Tetramethyl-8-trimethylsilanylethynyl-chroman-6-ylethynyl)-phenyl]-acetic acid methyl ester (Compound 38)

A solution of 6-ethynyl-8-trimethylsilanylethylnyl-2,2,4,4-tetramethyl chroman (Compound 37, 0.19 g, 0.612 mmol) and 4-iodo phenyl acetic acid methyl ester (see U.S. Pat. No. 6,252,090, 0.169 g, 0.612 mmol) in triethyl amine (8 mL) was treated with copper(I)iodide (0.019 g, 0.1 mmol) and sparged with argon for 5 minutes.

Dichlorobis(triphenylphosphine)palladium(II) (0.07 g, 0.1 mmol) was added and the reaction mixture was stirred overnight at room temperature. It was diluted with diethyl ether and filtered over a bed of celite. The filtrate was evaporated in vacuo to a brown oil that was subjected to flash column chromatography over silica gel (230-400 mesh) using 2-10% ethyl acetate in hexane as the eluent to afford the title compound (0.25 g, 89%).

$^1$H NMR (300 MHz, CDCl$_3$): δ7.46–7.40 (m, 4H), 7.23 (d, 2H, J=8.0 Hz), 3.69 (s, 3H), 3.62 (s, 2H), 1.85 (s, 2H), 1.38 (s, 6H), 1.34 (s, 6H), 0.26 (s, 9H).

General Procedure K: [4-(8-Ethynyl-2,2,4,4-tetramethyl-chroman-6-ylethynyl)-phenyl]-acetic acid (Compound 40)

A solution of [4-(2,2,4,4-tetramethyl-8-trimethylsilanyl-ethynyl-chroman-6-ylethynyl)-phenyl]-acetic acid methyl ester (Compound 38, 0.13 g, 0.28 mmol) in a mixture of methanol (3 mL), tetrahydrofuran (3 mL) and water (1.5 mL) was treated with lithium hydroxide monohydrate (0.13 g, 3.1 mmol) and the resulting reaction mixture was stirred at ambient temperature for 2.5 h. The volatiles were distilled off in vacuo and the residue was diluted with water and saturated aqueous ammonium chloride solution and extracted with ethyl acetate (×3). The combined organic phase was dried over anhydrous sodium sulfate, filtered and evaporated in vacuo to afford the title compound as a white solid (0.078 g, 74%).

$^1$H NMR (300 MHz, CDCl$_3$): δ7.50–7.45 (m, 4H), 7.27 (d, 2H, J=8.0 Hz), 3.67 (s, 2H), 3.24 (s, 1H), 1.88 (s, 2H), 1.41 (s, 6H), 1.37 (s, 6H).

[2-Fluoro-4-(2,2,4,4-tetramethyl-8-trimethylsilanyl-ethynyl-chroman-6-ylethynyl)-phenyl]-acetic acid methyl ester (Compound 39)

Following general procedure J and using 6-ethynyl-8-trimethylsilanylethylnyl-2,2,4,4-tetramethyl chroman (Compound 37, 0.1 g, 0.32 mmol), 2-fluoro-4-iodo phenyl acetic acid methyl ester (see U.S. Pat. No. 6,252,090, 0.095 g, 0.32 mmol), triethyl amine, copper(I)iodide (0.019 g, 0.1 mmol) and dichlorobis(triphenylphosphine)palladium(II) (0.071 g, 0.1 mmol), followed by flash column chromatography over silica gel (230-400 mesh) using 4-10% ethyl acetate in hexane as the eluent, the title compound was obtained as an oil (0.11 g, 72%).

$^1$H NMR (300 MHz, CDCl$_3$): δ7.44 (d, 1H, J=2.0 Hz), 7.40 (d, 1H, J=2.0 Hz), 7.36–7.18 (m, 3H), 3.71 (s, 3H), 3.68 (s, 2H), 1.88 (s, 2H), 1.39 (s, 6H), 1.35 (s, 6H), 0.26 (s, 9H).

[4-(8-Ethynyl-2,2,4,4-tetramethyl-chroman-6-ylethynyl)-2-fluoro-phenyl]-acetic acid (Compound 41)

Following general procedure K and using [2-fluoro-4-(2,2,4,4-tetramethyl-8-trimethylsilanylethynyl-chroman-6-ylethynyl)-phenyl]-acetic acid methyl ester (Compound 39, 0.11 g, 0.23 mmol), methanol, tetrahydrofuran, water and lithium hydroxide monohydrate followed by recrystallization from hot acetonitrile, the title compound was obtained as a pale yellow solid (0.045 g, 50%).

$^1$H NMR (300 MHz, CDCl$_3$): δ7.48 (d, 1H, J=2.0 Hz), 7.44 (d, 1H, J=2.0 Hz), 7.28–7.21 (m, 3H), 3.74 (s, 2H), 3.24 (s, 1H), 1.88 (s, 2H), 1.42 (s, 6H), 1.38 (s, 6H).

6-Trimethylsilanylethynyl-2,2,4,4-tetramethyl chroman-8-carbaldehyde (Compound 43)

Following general procedure I and using 6-bromo-2,2,4,4-tetramethyl chroman-8-carbaldehyde (Compound 42, see U.S. Pat. No. 6,303,785, 1.78 g, 5.4 mmol), triethyl amine (5 mL), tetrahydrofuran (10 mL), copper(I)iodide (0.23 g, 1.2 mmol), trimethylsilyl acetylene (3.3 mL, 23 mmol) and dichlorobis(triphenylphosphine)palladium(II) (0.843 g, 1.2 mmol) followed by flash column chromatography over silica gel (230-400 mesh) using 5% ethyl acetate in hexane as the eluent, the title compound (1.77 g, 99%) was obtained as a pale yellow solid.

$^1$H NMR (300 MHz, CDCl$_3$): δ10.33 (s, 1H), 7.70 (d, 1H, J=1.0 Hz), 7.51 (d, 1H, J=1.0 Hz), 1.81 (s, 2H), 1.33 (s, 6H), 1.29 (s, 6H), 0.10 (s, 9H).

6-Ethynyl-2,2,4,4-tetramethyl chroman-8-carbaldehyde (Compound 44)

A solution of 6-trimethylsilanylethynyl-2,2,4,4-tetramethyl chroman (Compound 43, 1.78 g, 5.4 mmol) in methanol (20 mL) was treated with potassium carbonate (0.745 g, 5.4 mmol) and the resulting reaction mixture was stirred at ambient temperature for 3 h. The reaction mixture was filtered, the filtrate was evaporated in vacuo and the residue was subjected to flash column chromatography over silica gel (230-400 mesh) using 2-5% ethyl acetate in hexane as the eluent to afford the title compound (1.1 g, 85%).

$^1$H NMR (300 MHz, CDCl$_3$): δ10.41 (s, 1H), 7.79 (d, 1H, J=1.8 Hz), 7.61 (d, 1H, J=1.8 Hz), 3.01 (s, 1H), 1.89 (s, 2H), 1.42 (s, 6H), 1.37 (s, 6H).

{4-[8-Formyl-2,2,4,4-tetramethyl chroman-6-ylethynyl]-phenyl}-acetic acid methyl ester (Compound 45)

Following general procedure J and using 6-ethynyl-2,2,4,4-tetramethyl chroman-8-carbaldehyde (Compound 44, 0.39 g, 1.61 mmol), 4-iodo phenyl acetic acid methyl ester (0.444 g, 1.61 mmol), triethyl amine (10 mL), copper(I) iodide (0.025 g, 0.13 mmol) and dichlorobis(triphenylphosphine)palladium(II) (0.090 g, 0.13 mmol) followed by flash column chromatography over silica gel (230-400 mesh)

using 5-20% ethyl acetate in hexane as the eluent the title compound was obtained as an oil (0.5 g, 80%).

$^1$H NMR (300 MHz, CDCl$_3$): δ10.42 (s, 1H), 7.81 (d, 1H, J=2.1 Hz), 7.64 (d, 1H, J=2.1 Hz), 7.45 (d, 2H, J=8.3 Hz), 7.24 (d, 2H, J=8.3 Hz), 3.68 (s, 3H), 3.62 (s, 2H), 1.88 (s, 2H), 1.41 (s, 6H), 1.37 (s, 6H).

{4-[8-Hydroxymethyl-2,2,4,4-tetramethyl-chroman-6-ylethynyl]-phenyl}-acetic acid methyl ester (Compound 46)

A stirred, cooled (ice bath) solution of {4-[8-formyl-2,2,4,4-tetramethyl chroman-6-ylethynyl]-phenyl}-acetic acid methyl ester (Compound 45, 0.21 g, 0.58 mmol) in methanol (4 mL) was treated with sodium borohydride (0.024 g, 0.64 mmol) and the resulting reaction mixture was stirred for 2 h. The reaction mixture was quenched with water and extracted with diethyl ether. The organic phase was washed with water (×1) and brine (×1), dried over anhydrous sodium sulfate, filtered and evaporated in vacuo to afford the title product as a colorless oil (0.21 g, 100%).

$^1$H NMR (300 MHz, CDCl$_3$): δ7.45 (d, 2H, J=7.8 Hz), 7.40 (d, 1H, J=2.2 Hz), 7.27 (d, 1H, J'2.2 Hz), 7.22 (d, 2H, J=7.8 Hz), 4.60 (s, 2H), 3.67 (s, 3H), 3.60 (s, 2H), 1.82 (s, 2H), 1.35 (s, 6H), 1.34 (s, 6H).

{4-[8-Bromomethyl-2,2,4,4-tetramethyl-chroman-6-ylethynyl]-phenyl}-acetic acid methyl ester (Compound 47)

A stirred, cooled (ice bath) solution of {4-[8-hydroxymethyl-2,2,4,4-tetramethyl-chroman-6-ylethynyl]-phenyl}-acetic acid methyl ester (Compound 46, 0.53 g, 0.58 mmol) and triphenylphosphine (0.198 g, 0.75 mmol) in anhydrous dichloromethane (5 mL) was treated with N-bromo succinimide (0.134 g, 0.75 mmol) under argon and the resulting reaction mixture was allowed to warm to ambient temperature and stirred overnight. The reaction mixture was quenched with dilute, aqueous sodium bicarbonate solution and extracted with diethyl ether. The organic phase was washed with water and brine, dried over anhydrous magnesium sulfate, filtered and evaporated in vacuo to a residue that on flash column chromatography over silica gel (230-400 mesh) using 4-10% ethyl acetate in hexane as the eluent afforded the title compound (0.19 g, 80%) as a colorless oil.

$^1$H NMR (300 MHz, CDCl$_3$): δ7.47 (d, 2H, J=8.1 Hz), 7.43 (d, 1H, J=2.1 Hz), 7.35 (d, 1H, J=2.1 Hz), 7.26 (d, 2H, J=8.2 Hz), 4.51 (s, 2H), 3.70 (s, 3H), 3.63 (s, 2H), 1.86 (s, 2H), 1.40 (s, 6H), 1.36 (s, 6H).

{4-[2,2,4,4-Tetramethyl-8-(3-trimethylsilanyl-prop-2-ynyl)-chroman-6-ylethynyl]-phenyl}-acetic acid methyl ester (Compound 48)

A solution of {4-[8-bromomethyl-2,2,4,4-tetramethyl-chroman-6-ylethynyl]-phenyl}-acetic acid methyl ester (Compound 47, 1.1 g, 2.4 mmol) in triethyl amine (2 mL) and N,N-dimethylformamide (10 mL) was sparged with argon and treated with trimethylsilylacetylene (2 mL, 14.1 mmol) and dichlorobis(triphenylphosphine)palladium(II) (0.135 g, 0.192 mmol). The resulting reaction mixture was heated at 95° C. for 20 h at the end of which it was cooled to ambient temperature and subjected to flash column chromatography over silica gel (230-400 mesh) using 1-7% ethyl acetate in hexane as the eluent to afford the title compound as an oil (0.715 g, 63%). $^1$H NMR (300 MHz, CDCl$_3$): δ7.49 (d, 1H, J=2.1 Hz), 7.47 (d, 2H, J=8.2 Hz), 7.37 (d, 1H, J=2.1 Hz), 7.25 (d, 2H, J=8.2 Hz), 3.70 (s, 3H), 3.63 (s, 2H) 3.55 (s, 2H), 1.83 (s, 2H), 1.35 (s, 6H), 1.34 (s, 6H), 0.20 (s, 9H).

[4-(2,2,4,4-Tetramethyl-8-prop-2-ynyl-chroman-6-ylethynyl)-phenyl-acetic acid (Compound 49)

Following general procedure K and using {4-[2,2,4,4-tetramethyl-8-(3-trimethylsilanyl-prop-2-ynyl)-chroman-6-ylethynyl]-phenyl}-acetic acid methyl ester (Compound 48, 0.105 g, 0.21 mmol), methanol (3 mL), tetrahydrofuran (3 mL), water (1.5 mL) and lithium hydroxide monohydrate (0.128 g, 3.07 mmol), the title compound was obtained as a pale yellow solid (0.077 g, 95%). $^1$H NMR (300 MHz, CDCl$_3$): δ7.51 (d, 1H, J=2.2 Hz), 7.49 (d, 2H, J=8.2 Hz), 7.39 (d, 1H, J=2.2 Hz), 7.25 (d, 2H, J=8.2 Hz), 3.66 (s, 2H), 3.52 (d, 2H, J=2.6 Hz), 2.61 (t, 1H, J=2.6 Hz), 1.83 (s, 2H), 1.36 (s, 6H), 1.35 (s, 6H).

Ethyl-8-cyano-2,2,4,4-tetramethyl chroman-6-carboxylate (Compound 29)

A solution of ethyl-8-iodo-2,2,4,4-tetramethyl chroman-6-carboxylate (Compound 24, 0.5 g, 1.29 mmol) and copper (I)cyanide (0.22 g, 2.58 mmol) in anhydrous DMF (4 ml) was heated to 160° C. overnight. It was then cooled to ambient temperature. Water was added and the reaction mixture was extracted with ether. The combined organic extract was washed with water, brine, dried over Na$_2$SO$_4$ and concentrated to give a crude residue. The residue was subjected to flash column chromatography over silica gel (230-400 mesh) using 5% to 10% ethyl acetate in hexane as the eluent to afford the title compound (0.3 g, 80%).

$^1$H NMR (300 MHz, CDCl$_3$): δ8.12 (d, 1H, J=2.1 Hz), 8.04 (d, 1H, J=2.1 Hz), 4.33 (q, 2H, J=7.0 Hz), 1.89 (s, 2H), 1.41 (s, 6H), 1.36 (s, 6H), 1.38–1.34 (m, 3H).

8-Cyano-2,2,4,4-tetramethyl chroman-6-carboxylic acid (Compound 30)

A solution of ethyl-8-cyano-2,2,4,4-tetramethylchroman-6-carboxylate (Compound 29, $^{1.36}$ g, 4.73 mmol) in ethanol (14 mL) was treated with 3N aqueous sodium hydroxide solution (3 mL, 15 mmol) and was stirred at ambient temperature for 3 h. The resulting solution was adjusted to pH~5 with 10% aqueous hydrochloric acid and extracted with ethyl acetate. The organic phase was dried over anhydrous magnesium sulfate, filtered and evaporated in vacuo to afford the title product as a white solid (1.15 g, 94%).

$^1$H NMR (300 MHz, CDCl$_3$): δ8.23 (d, 1H, J=2.1 Hz), 8.16 (d, 1H, J=2.1 Hz), 1.94 (s, 2H), 1.47 (s, 6H), 1.42 (s, 6H).

8-Cyano-2,2,4,4-tetramethyl chroman-6-carboxylic acid-3-fluoro-4-tert-butoxycarbonylmethyl-phenyl ester (Compound 31)

A solution of 8-cyano-2,2,4,4-tetramethyl chroman-6-carboxylic acid (Compound 30, 0.055 g, 0.19 mmol) in anhydrous dichloromethane (3 mL) was treated with tert-butyl-2-fluoro-4-hydroxy phenyl acetate (Compound 14, 0.052 g, 0.22 mmol), followed by 1-(3-dimethylaminopropyl)-3-ethylcarbodiimide hydrochloride (0.55 g, 0.29 mmol) and 4-(dimethylamino)pyridine (0.046 g, 0.38 mmol). The resulting solution was stirred at ambient temperature overnight. The reaction mixture was diluted with dichloromethane, washed with water and brine (×1), dried over anhydrous magnesium sulfate, filtered and evaporated in vacuo. The residue was subjected to flash column chromatography over silica gel (230-400 mesh) using 5% to 15% ethyl acetate in hexane as the eluent to afford the title compound as a white solid (0.085 g, 95%).

$^1$H NMR (300 MHz, CDCl$_3$): δ8.26 (d, 1H, J=2.1 Hz), 8.21 (d, 1H, J=2.1 Hz), 7.31 (t, 1H, J=7.9 Hz), 6.96-7.00 (m, 2H), 3.59 (s, 2H), 1.94 (s, 2H), 1.46 (s, 6H), 1.45 (s, 9H), 1.42 (s, 6H).

8-Cyano-2,2,4,4-tetramethyl-chroman-6-carboxylic acid-4-carboxymethyl-3-fluoro-phenyl ester (Compound 32)

A solution of 8-cyano-2,2,4,4-tetramethyl chroman-6-carboxylic acid-3-fluoro-4-tert-butoxycarbonylmethyl-phenyl ester (Compound 31, 0.084 g, 0.18 mmol) in 1,4-dioxane (4 mL) and THF (2 mL) was treated with formic acid (15 mL) at ambient temperature. After 2 h, the reaction mixture was diluted with water and extracted with diethyl ether. The organic phase was dried over anhydrous magnesium sulfate, filtered and evaporated in vacuo to afford the title product (0.055 g, 74%).

$^1$H NMR (300 MHz, CDCl$_3$): δ8.27 (d, 1H, J=2.1 Hz), 8.22 (d, 1H, J=2.0 Hz), 7.34 (t, 1H, J=7.9 Hz), 6.99-7.04 (m, 2H), 3.74 (s, 2H), 1.96 (s, 2H), 1.48 (s, 6H), 1.43 (s, 6H).

8-Cyano-2,2,4,4-tetramethyl-chroman-6-carboxylic acid 4-acetoxymethoxycarbonylmethyl-3-fluoro-phenyl ester (Compound 33)

A solution of 8-cyano-2,2,4,4-tetramethyl chroman-6-carboxylic acid (Compound 30, 1.15 g, 4.44 mmol) in anhydrous dichloromethane (20 mL) was treated with acetoxymethyl-2-fluoro-4-hydroxy phenyl acetate (Compound 21, 1.02 g, 4.22 mmol) followed by 1-(3-dimethylaminopropyl)-3-ethylcarbodiimide hydrochloride (1.28 g, 6.66 mmol) and 4-(dimethylamino)pyridine (1.08 g, 8.88 mmol). The resulting solution was stirred at ambient temperature overnight. The reaction mixture was diluted with dichloromethane, washed with water and brine (×1), dried over anhydrous magnesium sulfate, filtered and evaporated in vacuo. The residue was subjected to flash column chromatography over silica gel (230-400 mesh) using 20% to 30% ethyl acetate in hexane as the eluent to afford the title compound as a white solid (1.74 g, 85%).

$^1$H NMR (300 MHz, CDCl$_3$): δ8.27 (d, 1H, J=2.1 Hz), 8.23 (d, 1H, J=2.1 Hz), 7.34 (t, 1H, J=7.9 Hz), 7.03-6.99 (m, 2H), 5.79 (s, 2H), 3.75 (s, 2H), 2.12 (s, 3H), 1.96 (s, 2H), 1.48 (s, 6H), 1.43 (s, 6H).

What is claimed is:
1. A compound of the formula

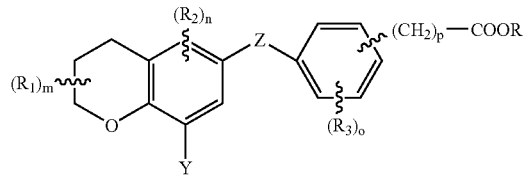

wherein Z is C≡C;
R$_1$ is alkyl having 1 to 6 carbons;
R$_2$ is independently alkyl of 1 to 6 carbons, F, Cl, Br, I, CF$_3$, fluoro substituted alkyl of 1 to 6 carbons, OH, SH, alkoxy of 1 to 6 carbons or alkylthio of 1 to 6 carbons;
R$_3$ is independently alkyl of 1 to 6 carbons, F, Cl, Br, I, CF$_3$, fluoro substituted alkyl of 1 to 6 carbons, OH, SH, alkoxy of 1 to 6 carbons or alkylthio of 1 to 6 carbons;
m is an integer having the values of 0 to 6;
n is an integer having the values of 0 to 2;
o is an integer having the values 0 to 4;
p is an integer having the values 0, 1, or 2;
Y is CH≡C—, CH≡C—CH$_2$—; CH$_2$=CH— or —C≡N;
R is is H, alkyl of 1 to 6 carbons, —CH$_2$OR$_4$, —CH$_2$—O—COR$_4$, or a cation of a pharmaceutically acceptable base, and
R$_4$ is alkyl having 1 to 6 carbons.

2. A compound in accordance with claim 1 where Y is CN.
3. A compound in accordance with claim 2 where p is one (1).
4. A compound in accordance with claim 1 wherein R$_1$ is methyl and m is 4.
5. A compound in accordance with claim 4 wherein the methyl groups are attached to the 2,2 and 4,4 positions of the chroman ring.
6. A compound in accordance with claim 1 wherein the R$_2$ group is alkyl or halogen and n is 1 or 2.
7. A compound in accordance with claim 1 wherein n is zero.
8. A compound in accordance with claim 1 wherein the phenyl group is 1,4 (para) substituted with the chroman-6-yl-ethynyl and (CH$_2$)$_p$COOR groups.
9. A compound in accordance with claim 8 wherein o is zero, or o is one (1) and R$_3$ is halogen or alkyl.
10. A compound in accordance with claim 9 wherein o is one (1) and R$_3$ is fluoro and the fluoro group is located in 1,2 (ortho) position relative to the (CH$_2$)$_p$COOR group.
11. A compound in accordance with claim 1 wherein o is zero, or o is one (1) and R$_3$ is halogen or alkyl.
12. A compound in accordance with claim 1 wherein Y is CH≡C—.
13. A compound in accordance with claim 12 wherein p is one (1).
14. A compound in accordance with claim 1 wherein Y is CH≡C—CH$_2$—.
15. A compound in accordance with claim 14 wherein p is one (1).
16. A compound of the formula

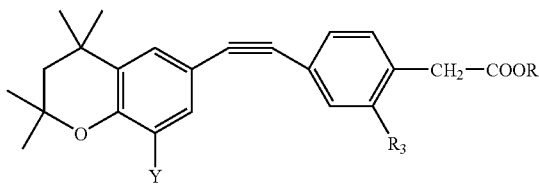

wherein Y is CH≡C— or CH≡C—CH$_2$—;
R$_3$ is H or F;
R is H, alkyl of 1 to 6 carbons, —CH$_2$OR$_4$, —CH$_2$—O—COR$_4$, or a cation of a pharmaceutically acceptable base, and
R$_4$ is alkyl having 1 to 6 carbons.

17. A compound in accordance with claim 16 where Y is CH≡C—.
18. A compound in accordance with claim 17 wherein R$_3$ is H.
19. A compound in accordance with claim 18 wherein R is H, or a cation of a pharmaceutically acceptable base.

20. A compound in accordance with claim 18 wherein R is methyl.

21. A compound in accordance with claim 17 wherein $R_3$ is F.

22. A compound in accordance with claim 21 wherein R is H, or a cation of a pharmaceutically acceptable base.

23. A compound in accordance with claim 16 wherein R is methyl.

24. A compound in accordance with claim 16 where Y is CH≡C—CH$_2$—.

25. A compound in accordance with claim 24 where $R_3$ is H.

26. A compound in accordance with claim 25 wherein R is H, or a cation of a pharmaceutically acceptable base.

27. A compound in accordance with claim 25 wherein R is methyl.

28. A compound of the formula

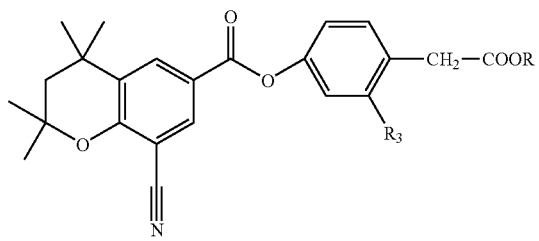

wherein $R_3$ is H or F;
R is H, alkyl of 1 to 6 carbons, —CH$_2$OR$_4$, —CH$_2$—O—COR$_4$, or a cation of a pharmaceutically acceptable base, and
$R_4$ is alkyl having 1 to 6 carbons.

29. A compound in accordance with claim 28 wherein $R_3$ is F.

30. A compound in accordance with claim 29 wherein R is H, or a cation of a pharmaceutically acceptable base.

31. A compound in accordance with claim 30 wherein R is CH$_2$OCOCH3.

32. A pharmaceutical composition for administration to a mammal, comprising a pharmaceutically acceptable excipient and an effective dose of one or more compounds in accordance with the formula below, to inhibit the enzyme cytochrome P450RAI in said mammal in need of such inhibition

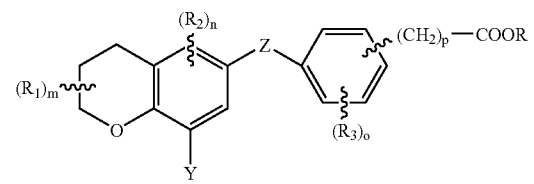

wherein Z is COO or C≡C;
$R_1$ is alkyl having 1 to 6 carbons;
$R_2$ is independently alkyl of 1 to 6 carbons, F, Cl, Br, I, CF$_3$, fluoro substituted alkyl of 1 to 6 carbons, OH, SH, alkoxy of 1 to 6 carbons or alkylthio of 1 to 6 carbons;
$R_3$ is independently alkyl of 1 to 6 carbons, F, Cl, Br, I, CF$_3$, fluoro substituted alkyl of 1 to 6 carbons, OH, SH, alkoxy of 1 to 6 carbons or alkylthio of 1 to 6 carbons;
m is an integer having the values of 0 to 6;
n is an integer having the values of 0 to 2;
o is an integer having the values 0 to 4;
p is an integer having the values 0, 1, or 2;
Y is CH≡C—, CH≡C—CH$_2$—; CH$_2$=CH— or —C≡N;
R is H, alkyl of 1 to 6 carbons, —CH$_2$OR$_4$, —CH$_2$—O—COR$_4$, or a cation of a pharmaceutically acceptable base, and
$R_1$ is alkyl having 1 to 6 carbons.

33. A pharmaceutical composition in accordance with claim 32 wherein in the formula of the compound Z is COO.

34. A pharmaceutical composition in accordance with claim 33 wherein the compound has the formula

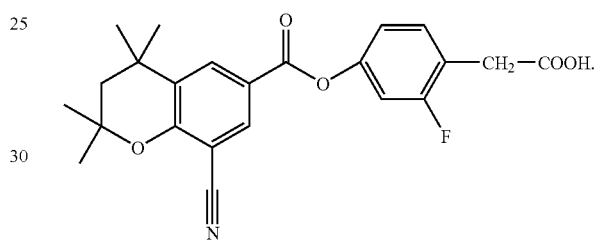

35. A pharmaceutical composition in accordance with claim 33 wherein the compound has the formula

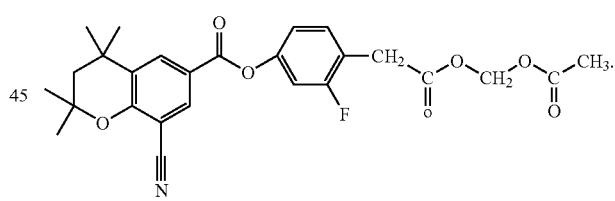

36. A pharmaceutical composition in accordance with claim 32 wherein the compound has the formula

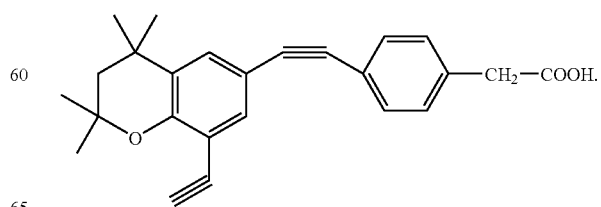

37. A pharmaceutical composition in accordance with claim 32 wherein the compound has the formula
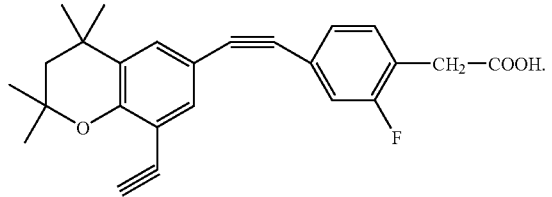
38. A pharmaceutical composition in accordance with claim 32 wherein the compound has the formula
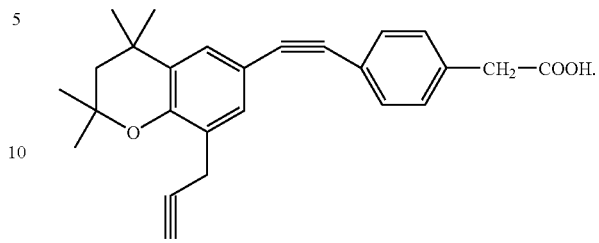
* * * * *